(12) United States Patent
Nomura et al.

(10) Patent No.: US 9,943,474 B2
(45) Date of Patent: Apr. 17, 2018

(54) WATER-BASED COSMETIC

(71) Applicant: The Nisshin OilliO Group, Ltd., Tokyo (JP)

(72) Inventors: Aki Nomura, Yokohama (JP); Hisanori Kachi, Yokohama (JP); Makoto Matsuzawa, Yokohama (JP); Hiromu Tokura, Yokohama (JP); Minaho Komori, Yokohama (JP)

(73) Assignee: The Nisshin OilliO Group, Ltd., Tokyo (JP)

( * ) Notice: Subject to any disclaimer, the term of this patent is extended or adjusted under 35 U.S.C. 154(b) by 0 days.

(21) Appl. No.: 15/696,644

(22) Filed: Sep. 6, 2017

(65) Prior Publication Data

US 2017/0367960 A1 Dec. 28, 2017

Related U.S. Application Data

(63) Continuation of application No. PCT/JP2016/056607, filed on Mar. 3, 2016.

(30) Foreign Application Priority Data

Mar. 10, 2015 (JP) ................................ 2015-046976

(51) Int. Cl.
| | | |
|---|---|---|
| *A61K 8/73* | (2006.01) | |
| *A61K 8/81* | (2006.01) | |
| *A61K 8/63* | (2006.01) | |
| *A61K 8/92* | (2006.01) | |
| *A61K 8/31* | (2006.01) | |
| *A61K 8/37* | (2006.01) | |
| *A61K 8/60* | (2006.01) | |
| *A61K 8/86* | (2006.01) | |
| *A61K 8/06* | (2006.01) | |
| *A61K 8/46* | (2006.01) | |
| *A61K 8/34* | (2006.01) | |
| *A61Q 19/00* | (2006.01) | |

(52) U.S. Cl.
CPC ................ *A61K 8/73* (2013.01); *A61K 8/062* (2013.01); *A61K 8/31* (2013.01); *A61K 8/345* (2013.01); *A61K 8/37* (2013.01); *A61K 8/463* (2013.01); *A61K 8/60* (2013.01); *A61K 8/63* (2013.01); *A61K 8/731* (2013.01); *A61K 8/733* (2013.01); *A61K 8/8111* (2013.01); *A61K 8/8129* (2013.01); *A61K 8/8147* (2013.01); *A61K 8/8152* (2013.01); *A61K 8/86* (2013.01); *A61K 8/922* (2013.01); *A61K 8/925* (2013.01); *A61Q 19/00* (2013.01); *A61K 2800/54* (2013.01)

(58) Field of Classification Search
None
See application file for complete search history.

(56) References Cited

U.S. PATENT DOCUMENTS 9,125,839 B2 * 9/2015 Kachi ..................... A61K 8/06

FOREIGN PATENT DOCUMENTS

| JP | 2005053835 A | 3/2005 |
|---|---|---|
| JP | 2013139423 A | 7/2013 |
| JP | 2014031328 A | 2/2014 |
| JP | 2014181224 A | 9/2014 |
| WO | 2011111854 A1 | 9/2011 |

OTHER PUBLICATIONS

PCT Office, International Search Report issued in PCT/JP2016/056607 dated May 24, 2016, 4 pages.

\* cited by examiner

*Primary Examiner* — Brian J Davis
(74) *Attorney, Agent, or Firm* — Wood Herron & Evans LLP

(57) ABSTRACT

A water-based cosmetic including:
  agar having a weight average molecular weight of 10,000 to 60,000 (component (A));
  xanthan gum (component (B)); and
  a water-soluble polymer excluding the component (A) or (B) (component (C)).

8 Claims, No Drawings

WATER-BASED COSMETIC

TECHNICAL FIELD

The present invention relates to a water-based cosmetic that exhibits excellent scoopability with a finger, provides excellent feeling of richness and moist feeling while providing a highly fresh tactile sensation at the time of application with no sliminess or stickiness, and provides a feeling of compatibility, as if to blend in, with the skin (skin compatibility).

Priority is claimed on Japanese Patent Application No. 2015-046976, filed Mar. 10, 2015, the content of which is incorporated herein by reference.

BACKGROUND ART

In water-based cosmetics such as aqueous cosmetics and oil-in-water emulsified cosmetics, water-soluble thickeners have been conventionally used for the purpose of enhancing the storage stability and the purpose of adjusting the tactile sensation. Examples of the water-soluble thickener include natural plant polymers such as agar, guar gum, carrageenan and glucomannan, natural microbial polymers such as xanthan gum, succinoglycan and gellan gum, and semi-synthetic/synthetic polymers such as carboxyvinyl polymers, alkyl-modified carboxyvinyl polymers, hydroxyethyl cellulose and hydroxypropyl methyl cellulose, and studies for reforming cosmetics by combining these thickeners have been conventionally conducted.

For example, Patent Document 1 discloses an external composition for skin obtained by combining agar having a weight average molecular weight (weight average molecular weight of 10,000 to 60,000) smaller than that of ordinary agar with xanthan gum at a specific ratio that is excellent in storage stability, extensibility to the skin and compatibility with the skin, can eliminate the sliminess originating from xanthan gum, does not generate scum-like residues, and can reduce the lubricity when moisture readheres to the fingers used for application.

In addition, Patent Document 2 discloses an emulsion-type external preparation for skin obtained by using a polysaccharide-based polymer and an acrylic polymer in combination that exhibits favorable storage stability even when carnitine or a salt thereof is blended, has no stickiness, and provides the skin with an excellent tactile sensation.

Furthermore, Patent Document 3 discloses a cosmetic obtained by dispersing agar gel particles containing a powder in an aqueous medium containing one or two or more selected from carboxyvinyl polymers and alkyl-modified carboxyvinyl polymers and natural gums in which the agar gel particles easily disintegrate while leaving no residues, combine with the aqueous medium and uniformly spread onto the skin, and exhibit excellent compatibility with the skin.

CITATION LIST

Patent Documents

[Patent Document 1] International Publication No. 2011/111854
[Patent Document 2] Japanese Unexamined Patent Application, First Publication No. 2005-053835
[Patent Document 3] Japanese Unexamined Patent Application, First Publication No. 2014-181224

SUMMARY OF INVENTION

Technical Problem

In the cosmetics described in Patent Documents 1 to 3, although improvements have been made in terms of the storage stability, the lack of stickiness and the uniform coating properties, the ease of scooping (scoopability) of the cosmetic with a finger is not good, which leads to a problem of stress at the time of use. On the other hand, if the added amount of the water-soluble thickener is increased in an attempt to improve the ease of scooping out with a finger, problems arise in that the tactile sensation at the time of application is significantly deteriorated, the feeling of richness and the moist feeling become excessive, stickiness occurs, and a very heavy feeling occurs at the time of application.

The present invention has an object of providing a water-based cosmetic that exhibits excellent scoopability with a finger (that is, ease of scooping with a finger), provides a feeling of richness and a moist feeling as well as a feeling of freshness at the time of use, and provides a feeling of compatibility, as if to blend in, with the skin (hereinafter may be referred to as "skin compatibility").

Solution to Problem

As a result of extensive investigations in order to solve the above problems, the inventors of the present invention have found that by combining agar having a weight average molecular weight of 10,000 to 60,000, xanthan gum and a water-soluble polymer, both the tactile sensation such as the freshness at the time of application to the skin and the scoopability with a finger can be improved, which has led to the completion of the present invention.

That is, the water-based cosmetic according to the present invention includes the following aspects [1] to [9].

[1] A water-based cosmetic characterized by consisting of:
a component (A) including agar having a weight average molecular weight of 10,000 to 60,000;
a component (B) including xanthan gum; and
a component (C) including a water soluble polymer (excluding the component (A) or (B)).

[2] The water-based cosmetic according to the above [1], wherein a content ratio of the aforementioned component (A) to the aforementioned component (B) is from 4:6 to 8:2 in mass ratio,
a content ratio of the total amount of the aforementioned component (A) and the aforementioned component (B) to the aforementioned component (C) is from 1:5 to 15:1 in mass ratio,
a content of the aforementioned component (A) is from 0.01 to 2% by mass of the entire cosmetic,
a content of the aforementioned component (B) is from 0.01 to 2% by mass of the entire cosmetic, and
a content of the aforementioned component (C) is from 0.01 to 2% of the entire cosmetic.

[3] The water-based cosmetic according to the above [1] or [2], further including a component (D) including a moisturizing agent in an amount of 3 to 30% by mass of the entire cosmetic.

[4] The water-based cosmetic according to any one of the above [1] to [3], further including a component (E) including a nonionic surfactant in an amount of 0.01 to 40% by mass of the entire cosmetic.

[5] The water-based cosmetic according to any one of the above [1] to [4], further including a component (F) including an oil agent in a liquid form at 25° C. in an amount of 0.01 to 50% by mass of the entire cosmetic.

[6] The water-based cosmetic according to any one of the above [1] to [5], further including a component (G) including an oil agent in a paste form at 25° C. in an amount of 0.01 to 10% by mass of the entire cosmetic. [7] The water-based cosmetic according to any one of the above [1] to [6], further including a component (H) including an oil agent in a solid form at 25° C. in an amount of 0.1 to 10% by mass of the entire cosmetic.

[8] The water-based cosmetic according to any one of the above [1] to [7], wherein the aforementioned component (C) is one or two or more selected from a carboxyvinyl polymer and an acrylic acid/alkyl methacrylate copolymer.

[9] The water-based cosmetic according to any one of the above [1] to [8], which is an oil-in-water type emulsion.

That is, the present invention includes the following aspects.

(1) A water-based cosmetic including:
agar having a weight average molecular weight of 10,000 to 60,000 (component (A));
xanthan gum (component (B)); and
a water-soluble polymer excluding the component (A) or (B) (component (C)).

(2) The water-based cosmetic according to (1),
wherein a ratio of a content of the aforementioned component (A) to a content of the aforementioned component (B) is from 4:6 to 8:2 in mass ratio;
a ratio of a total content of the aforementioned component (A) and the aforementioned component (B) to a content of the aforementioned component (C) is from 1:5 to 15:1 in mass ratio;
the content of the aforementioned component (A) is from 0.01 to 2% by mass with respect to a total mass of the aforementioned water-based cosmetic;
the content of the aforementioned component (B) is from 0.01 to 2% by mass with respect to the total mass of the aforementioned water-based cosmetic; and
the content of the aforementioned component (C) is from 0.01 to 2% by mass with respect to the total mass of the aforementioned water-based cosmetic.

(3) The water-based cosmetic according to (1) or (2), further including a moisturizing agent (component (D)) in an amount of 3 to 30% by mass with respect to the total mass of the aforementioned water-based cosmetic.

(4) The water-based cosmetic according to any one of (1) to (3), further including a nonionic surfactant (component (E)) in an amount of 0.01 to 40% by mass with respect to the total mass of the aforementioned water-based cosmetic.

(5) The water-based cosmetic according to any one of (1) to (4), further including an oil agent in a liquid form at 25° C. (component (F)) in an amount of 0.01 to 50% by mass with respect to the total mass of the aforementioned water-based cosmetic.

(6) The water-based cosmetic according to any one of (1) to (5), further including an oil agent in a paste form at 25° C. (component (G)) in an amount of 0.01 to 10% by mass with respect to the total mass of the aforementioned water-based cosmetic.

(7) The water-based cosmetic according to any one of (1) to (6), further including an oil agent in a solid form at 25° C. (component (H)) in an amount of 0.1 to 10% by mass with respect to the total mass of the aforementioned water-based cosmetic.

(8) The water-based cosmetic according to any one of (1) to (7), wherein the aforementioned component (C) is at least one selected from a carboxyvinyl polymer and an acrylic acid/alkyl methacrylate copolymer.

(9) The water-based cosmetic according to any one of (1) to (8), which is an oil-in-water type emulsion.

Advantageous Effects of Invention

According to the present invention, it is possible to provide a water-based cosmetic that exhibits excellent scoopability with a finger, provides excellent feeling of richness and moist feeling while providing a highly fresh tactile sensation at the time of application to the skin, and provides a feeling of compatibility, as if to blend in, with the skin.

DESCRIPTION OF EMBODIMENTS

In the present description, a water-based cosmetic is a cosmetic containing an aqueous component and has a property to disperse in water. The aqueous component is water and a component that is soluble in water. In addition, in the present invention, an inorganic water-soluble polymer having a water absorbing function is also handled as an aqueous component.

An oily component, a fine particle component, a surfactant or the like can be blended into the water-based cosmetic.

A water-based cosmetic containing an oily component has a property to disperse in water because the oily component is uniformly dispersed or solubilized in the aqueous component serving as a continuous layer.

A water-based cosmetic containing a fine particle component has a property to disperse in water since the fine particle component is dispersed in the aqueous component.

A water-based cosmetic containing a surfactant has a property to disperse in water since the surfactant is dispersed in the aqueous component.

Examples of the aqueous component include water, a water-soluble polymer and a moisturizing agent.

Examples of the oily component include an oil agent and the like.

Examples of the fine particle component include a pigment and a powder component.

Examples of the surfactant include an anionic surfactant, a cationic surfactant and an amphoteric surfactant.

The water-based cosmetic according to the present invention is characterized by including a component (A): agar having a weight average molecular weight of 10,000 to 60,000; a component (B): xanthan gum; and a component (C): a water soluble polymer (excluding the components (A) and (B)).

The agar having a weight average molecular weight of 10,000 to 60,000 (hereinafter may be referred to as "low molecular weight agar" in some cases) as the component (A) preferably has a weight average molecular weight of 20,000 to 60,000, more preferably from 30,000 to 60,000, still more preferably from 40,000 to 60,000, and even more preferably from 43,000 to 60,000. When agar having a weight average molecular weight of more than 60,000 is used, the water-based cosmetic lacks freshness and causes a feeling of stickiness when used. In particular, when the water-based cosmetic according to the present invention further contains a moisturizing agent as the component (D) to be described later, if agar having a weight average molecular weight of more than 60,000 is used, the effect of suppressing stickiness of the moisturizing agent cannot be achieved. That is, when agar having a weight average molecular weight of 60,000 or less is used, the water-based cosmetic provides freshness and suppresses the feeling of stickiness when used. In particular, when a moisturizing agent as the component (D) is contained, if agar having a weight average molecular weight of 60,000 or less is used, stickiness of the moisturizing agent can be suppressed.

The low molecular weight agar of the component (A) preferably has a narrow molecular weight distribution. The molecular weight distribution is given by the value (Mw/Mn) obtained by dividing the weight average molecular weight (Mw) of the agar by the number average molecular weight (Mn).

The number average molecular weight (Mn) is an average of the molecular weight per molecule. Therefore, if the molecular weight distribution is broad and the number of molecules having a small molecular weight increases, the number average molecular weight (Mn) decreases due to the influence thereof. On the other hand, the weight average molecular weight (Mw) is an average based on the weight fraction of molecules. Therefore, even if the molecular weight distribution is broad and the number of molecules having a small molecular weight increases, since the contribution of these low molecular components to the total weight is small, the change in the weight average molecular weight (Mw) is small. In other words, it is indicated that the smaller the value (Mw/Mn) obtained by dividing the weight average molecular weight (Mw) by the number average molecular weight (Mn), the narrower the molecular weight distribution, and the greater the value, the broader the molecular weight distribution.

In addition to having a low molecular weight, the low molecular agar used in the present invention preferably has a value of Mw/Mn indicating a molecular weight distribution of 1.1 to 8.0, more preferably from 1.5 to 7.0, still more preferably from 2.0 to 6.0, and most preferably from 2.5 to 5.5. When the molecular weight distribution is within this range, it is possible to obtain a water-based cosmetic that exhibits excellent scoopability with a finger (that is, ease of scooping with a finger), provides excellent feeling of richness and moist feeling while providing a highly fresh tactile sensation at the time of application with no sliminess or stickiness, and provides a feeling of compatibility, as if to blend in, with the skin. Especially when the water-based cosmetic according to the present invention further contains a moisturizing agent as the component (D) to be described later, by using low molecular weight agar having a molecular weight distribution within this range, it is possible to suppress the stickiness of the moisturizing agent in particular.

The weight average molecular weight and number average molecular weight of agar can be measured in accordance with the gel permeation chromatography method by HPLC. More specifically, for example, agar is dissolved in distilled water at 95 to 97° C. and then cooled to 50° C. to obtain a measurement sample. The measurement is conducted at a constant temperature (for example, 50 to 55° C.) using, as an example of a liquid chromatography apparatus, LC-10AT VP and a differential refractometer RID-10A as a detector, both of which are manufactured by Shimadzu Corporation, TOSOH TSK-GEL for HPLC, TSK-GEL GMPWXL or the like manufactured by Tosoh Corporation as a column, and 0.1 M sodium nitrate or the like as a developing solvent. In order to determine the weight average molecular weight and the number average molecular weight of agar, pullulan whose molecular weight is known (for example, Shodex STANDARD P-82) is used as a standard sample. The standard sample is dissolved in distilled water and subjected to a measurement by a gel permeation chromatography method using HPLC under the same conditions.

As a method for obtaining low molecular weight agar, for example, a method of cutting molecules of agar by an acid treatment and then removing the effect of the acid used in the acid treatment by a neutralization treatment can be mentioned. The agar used for the acid treatment may be agar obtained by redissolving agar which has undergone a dehydration step or a freezing/melting step during an extraction step, or may be a crushed agar in a dry state.

Alternatively, low molecular weight agar can also be produced from the beginning of production. It is also possible to perform an acid treatment during an agar production process, for example, during an extraction step, or on the agar that has undergone any of an extraction step or a filtration step. By adjusting the acid strength and the treatment time, it is possible to obtain low molecular weight agar which is reduced in molecular weight to a desired molecular weight. In addition, as low molecular weight agar, commercially available products such as "Ena" manufactured by Ina Food Industry Co., Ltd. can also be used.

Xanthan gum is a polysaccharide produced by *Xanthomonas campestris* and is widely used as a thickener for cosmetics and foods and in other fields. As the xanthan gum of the component (B), commercially available xanthan gum may be used as it is. For example, "NOMCORT Z" and "NOMCORT ZZ" manufactured by The Nisshin OilliO Group, Ltd., "KELTROL" manufactured by CP Kelco, and the like are suitably used.

The content ratio of the low molecular weight agar as the component (A) to the xanthan gum as the component (B) in the water-based cosmetic according to the present invention is preferably from 4:6 to 8:2 in mass ratio, more preferably from 4:6 to 7:3, still more preferably from 5:5 to 7:3, and even more preferably from 6:4 to 7:3. When the content ratio of the xanthan gum is higher than these ranges, the scoopability of the water-based cosmetic with a finger is poor, and stickiness and sliminess tend to occur easily. Further, when the content ratio of the low molecular weight agar is higher than these ranges, there will be no freshness and it causes a feeling of stickiness when used. In addition, the moist feeling also decreases. That is, when the content ratio of the xanthan gum is within the above range, the scoopability of the water-based cosmetic with a finger is favorable, and stickiness and sliminess are less likely to occur. In addition, when the content ratio of the low molecular weight agar is within the above range, the water-based cosmetic provides freshness, is unlikely to cause stickiness, and the moist feeling also improves.

The content of the low molecular weight agar as the component (A) of the water-based cosmetic according to the present invention is preferably from 0.01 to 2% by mass, more preferably from 0.1 to 2% by mass, still more preferably from 0.1 to 1% by mass, and particularly preferably from 0.18 to 0.6% by mass with respect to the total mass of the water-based cosmetic. The content of the xanthan gum as the component (B) of the water-based cosmetic according to the present invention is preferably from 0.01 to 2% by mass, more preferably from 0.1 to 2% by mass, still more preferably from 0.1 to 1% by mass, and particularly preferably from 0.12 to 0.4% by mass with respect to the total mass of the water-based cosmetic.

The total content of the low molecular weight agar as the component (A) and the xanthan gum as the component (B) in the water-based cosmetic according to the present invention is preferably from 0.01 to 10% by mass, more preferably from 0.1 to 5% by mass, still more preferably from 0.2 to 4% by mass, and particularly preferably from 0.3 to 1% by mass with respect to the total mass of the water-based cosmetic. When the total content of the component (A) and the component (B) is within this range, the effects of improving the scoopability with a finger and the skin compatibility will be sufficient. In addition, when the water-based cosmetic according to the present invention contains a moisturizing agent as the component (D) to be described later, the effect of suppressing stickiness of the moisturizing agent also increases. Furthermore, when the water-based cosmetic according to the present invention contains oil components of the components (F) to (H) to be described later, the effect of improving the emulsion stability also increases.

The water-soluble polymer (aqueous polymer) as the component (C) (excluding the components (A) and (B)) may be a natural water-soluble polymer, a semisynthetic water-soluble polymer, a synthetic water-soluble polymer or an inorganic water-soluble polymer. Further, the component (C) to be contained in the water-based cosmetic according to the present invention may be a single type of water-soluble polymer, or two or more types of water-soluble polymers may be used in combination.

Examples of the natural water-soluble polymers include plant polymers such as gum arabic, tragacanth gum, galactan, guar gum, carob gum, karaya gum, carrageenan, pectin, quince seeds (also called marmelo), algae colloids (also called brown algae extracts) and starches (rice, maize, potato and wheat); microbial polymers such as dextran, succinoglucan and pullulan; and animal polymers such as collagen, casein, albumin and gelatin.

Examples of the semisynthetic water-soluble polymer include starch-based polymers such as carboxymethyl starch and methylhydroxypropyl starch; cellulose-based polymers such as methyl cellulose, nitrocellulose, methylhydroxypropyl cellulose, sodium cellulose sulfate, hydroxyethyl cellulose, hydroxypropyl cellulose, hydroxypropylmethyl cellulose, carboxymethyl cellulose, sodium carboxymethyl cellulose, crystalline cellulose and cellulose powders; and alginate-based polymers such as sodium alginate and propylene glycol alginate.

Examples of the synthetic water-soluble polymer include vinyl polymers such as polyvinyl alcohols, polyvinyl methyl ethers and polyvinyl pyrrolidone; polyoxyethylene-based polymers such as polyethylene glycol 20,000, polyethylene glycol 40,000, polyethylene glycol 60,000, polyethylene glycol having an average degree of polymerization of 90,000 (PEG-90 M) and polyoxyethylene polyoxypropylene copolymers; acrylic polymers such as carboxyvinyl polymers (also referred to as carbopol), sodium polyacrylate, polyethyl acrylate, polyacrylamide, acrylic acid/alkyl methacrylate copolymers and acrylate copolymers; polyethyleneimines; and cationic polymers.

Examples of the inorganic water-soluble polymer include bentonite, AlMg silicate (veegum), laponite, hectorite and silicic acid anhydride.

As the water-soluble polymer of the component (C), at least one (one or two or more) selected from the group consisting of carboxyvinyl polymers, acrylic acid/alkyl methacrylate copolymers, acrylate copolymers, hydroxyethyl cellulose, hydroxypropylmethyl cellulose, polyvinyl alcohols, polyethylene glycol and sodium alginate is preferable, and at least one (one or two or more) selected from the group consisting of carboxyvinyl polymers and acrylic acid/alkyl methacrylate copolymers is particularly preferable, since a cosmetic with improved freshness with less sliminess and stickiness can be obtained.

The content of the water-soluble polymer as the component (C) in the water-based cosmetic according to the present invention is preferably from 0.01 to 2% by mass, more preferably from 0.01 to 1% by mass, still more preferably from 0.05 to 0.5% by mass, and particularly preferably from 0.1 to 0.5% by mass with respect to the total mass of the water-based cosmetic. When the content of the component (C) is within this range, a water-based cosmetic that provides a very favorable tactile sensation such as freshness at the time of application to the skin can be obtained.

The ratio of the total content of the components (A) and (B) to the content of the component (C) in the water-based cosmetic according to the present invention is preferably from 1:5 to 15:1 in mass ratio. When the ratio of the total content of the component (A) and the component (B) to the content of the component (C) is within this range, the effects of improving the scoopability with a finger and the skin compatibility will be sufficient.

In addition to the component (A), the component (B) and the component (C), the water-based cosmetic according to the present invention preferably further contains a moisturizing agent as the component (D).

Examples of the moisturizing agent as the component (D) include glycerin, diglycerin, propylene glycol (hereinafter sometimes abbreviated as PG), 1,3-propanediol, 1,3-butylene glycol, 3-methyl-1,3-butanediol, 1,2-pentanediol, dipropylene glycol (hereinafter sometimes abbreviated as DPG), 1,2-hexanediol, hexylene glycol, polyethylene glycol 1,000 (hereinafter sometimes abbreviated as PEG-20), PPG-10 methyl glucose ether, polyoxyethylene methyl glucoside, sorbitol, trehalose, erythritol, hyaluronic acid or a salt thereof, and pyrrolidonecarboxylic acid or a salt thereof.

Among the components described above, glycerin, diglycerin, dipropylene glycol, 1,3-propanediol, PEG-20, sorbitol, trehalose, hyaluronic acid or a salt thereof, PPG-10 methyl glucose ether, polyoxyethylene methyl glucoside and erythritol are preferable.

The component (D) to be contained in the water-based cosmetic according to the present invention may be a single type of moisturizing agent, or two or more types of moisturizing agents may be used in combination. When the water-based cosmetic according to the present invention contains a humectant as the component (D), the content of the component (D) is preferably from 3 to 30% by mass and more preferably from 6 to 16.5% by mass, with respect to the total mass of the water-based cosmetic.

The water-based cosmetic according to the present invention may further contain a surfactant in addition to the component (A), the component (B) and the component (C). It is possible to use at least one (that is, one or two or more) surfactant selected from the group consisting of an anionic surfactant, a cationic surfactant, an amphoteric surfactant and a nonionic surfactant in combination.

When the water-based cosmetic according to the present invention contains a surfactant, the content of the surfactant is preferably from 0.01 to 40% by mass, more preferably from 0.01 to 20% by mass, and still more preferably from 0.01 to 10% by mass with respect to the total mass of the water-based cosmetic.

If the water-based cosmetic according to the present invention contains a surfactant, it is preferable to contain a component (E) which is a nonionic surfactant. Examples of the nonionic surfactant as the component (E) include POE-sorbitan fatty acid esters such as POE-sorbitan monooleate, POE-sorbitan monostearate, POE-sorbitan tetraoleate, POE (20) sorbitan monococonut oil fatty acid and polysorbate 60; POE-sorbit fatty acid esters such as POE-sorbit monolaurate, POE-sorbit monooleate, POE-sorbit pentaoleate and POE-sorbit monostearate; POE-glycerin fatty acid esters such as POE-glycerin monostearate, POE-glycerin monoisostearate and POE-glycerin triisostearate (polyoxyethylene glyceryl triisostearate); POE-fatty acid esters such as POE-monooleate, PO-monostearate, POE-distearate, POE-dioleate and ethylene glycol distearate; POE-alkyl ethers such as POE-lauryl ether (Laureth-7), POE-oleyl ether, POE-stearyl ether (Steareth-20), POE-behenyl ether, POE-2-octyldodecyl ether and POE-cholestanol ether; Pluronic-type surfactants such as Pluronics; POE/POP-alkyl ethers such as POE/POP-cetyl ether, POE/POP-2-decyltetradecyl ether, POE/POP-monobutyl ether, POE/POP-hydrogenated lanolin and POE/POP-glycerin ether; tetra-POE/tetra-POP-ethylenediamine condensates such as Tetronic surfactants; POE-hydrogenated castor oil such as POE-castor oil and PEG-40 hydrogenated castor oil; POE-castor oil derivatives and POE-hydrogenated castor oil derivatives such as POE-hydrogenated castor oil monoisostearate, POE-hydrogenated castor oil triisostearate, POE-hydrogenated castor oil monopyroglutamic acid monoisostearic acid diester and POE-hydrogenated castor oil maleate; POE-beeswax/lanolin derivatives such as POE-sorbit beeswax; alkanolamides such as coconut oil fatty acid diethanolamide (cocamide DEA), lauric acid monoethanolamide and fatty acid isopropanolamide; polyglycerol fatty acid esters such as polyglyceryl caprylate, polyglyceryl sesquicaprylate, polyglyceryl dicaprylate, polyglyceryl monolaurate, polyglyceryl monostearate, polyglyceryl monooleate, polyglyceryl distearate and polyglyceryl dioleate; modified silicone such as PEG-11 methyl ether dimethicone and methyl polysiloxane/cetylmethyl polysiloxane/poly(oxyethylene/oxypropylene) methyl polysiloxane copolymers; sorbitan fatty acid esters such as sorbitan monooleate, sorbitan monoisostearate, sorbitan monolaurate, sorbitan monopalmitate, sorbitan monostearate, sorbitan sesquioleate, sorbitan sesquiisostearate, sorbitan trioleate, diglycerol sorbitan penta-2-ethylhexylate and diglycerol sorbitan tetra-2-ethylhexylate; glycerin fatty acid esters such as glyceryl monocotton seed oil fatty acid, glyceryl monoerucate, glyceryl sesquioleate, glyceryl monostearate, glyceryl α,α'-oleate pyroglutamate and glyceryl monooleate, and polyglycerol fatty acid esters such as diglyceryl monoisostearate, diglyceryl diisostearate, diglyceryl condensed ricinoleate and tetraglyceryl condensed ricinoleate; propylene glycol fatty acid esters such as propylene glycol monostearate; hydrogenated castor oil derivatives; glycerin alkyl ethers; decyl glucosides; cetearyl glucosides; POE-propylene glycol fatty acid esters; POE-alkylamines; POE-fatty acid amides; sucrose fatty acid esters; POE-nonylphenyl formaldehyde condensates; alkylethoxydimethylamine oxides; and trioleyl phosphate. Among these, POE-glycerin fatty acid esters, POE-hydrogenated castor oil, POE-alkyl ethers, POE-sorbitan fatty acid esters, cetearyl glucosides, modified silicone and polyglycerol fatty acid esters are preferable.

In the case where the water-based cosmetic according to the present invention contains a nonionic surfactant as the component (E), the content of the component (E) is preferably from 0.01 to 40% by mass, more preferably from 0.01 to 20% by mass, and still more preferably from 0.01 to 10% by mass with respect to the total mass of the water-based cosmetic.

The water-based cosmetic according to the present invention may further contain an oil agent in addition to the component (A), the component (B) and the component (C). The oil agent contained in the water-based cosmetic according to the present invention may be an oil agent in a liquid form at 25° C., an oil agent in a paste form at 25° C. or an oil agent in a solid form at 25° C. In addition, it is also possible to use these in combination.

Here, in the present invention, an oil agent in a liquid form at 25° C. is defined as a component (F), an oil agent in a paste form at 25° C. is defined as a component (G), and an oil agent in a solid form at 25° C. is defined as a component (H).

It should be noted that the expression "in a liquid form at 25° C." means that the oil agent exhibits fluidity at 25° C., the expression "in a paste form at 25° C." refers to an intermediate state between a liquid state and a solid state, and means that the oil agent exhibits no fluidity at 25° C. but exhibits fluidity when a force is applied at a certain level or higher, and the expression "in a solid form at 25° C." means that the oil agent is in a solid state at 25° C.

When the water-based cosmetic according to the present invention contains an oil agent, the water-based cosmetic is preferably an oil-in-water type emulsion.

When the water-based cosmetic according to the present invention contains an oil agent, the content of the oil agent is preferably from 0.01 to 50% by mass and more preferably from 0.1 to 25% by mass, with respect to the total mass of the water-based cosmetic.

When the water-based cosmetic according to the present invention contains an oil agent in a liquid form at 25° C. as the component (F), examples of the oil agent as the component (F) include hydrocarbon oils such as hydrogenated polydecene, hydrogenated polyisobutene, mineral oil and squalane; monohydric alcohol fatty acid esters such as lanolin acetate, cetyl 2-ethylhexanoate, ethylhexyl isononanoate, isononyl isononanoate, isodecyl isononanoate, isotridecyl isononanoate, cocoalkyl (caprylate/caprate), hexyldecyl dimethyloctanoate, hexyl laurate, myristyl myristate, isostearyl myristate, isopropyl myristate, octyldodecyl myristate, isopropyl palmitate, 2-ethylhexyl palmitate, butyl stearate, ethylhexyl stearate, isocetyl stearate, isopropyl isostearate, isocetyl isostearate, ethylhexyl hydroxystearate, ethylhexyl cocoate, decyl oleate, cetyl lactate, myristyl lactate, octyldodecyl lactate, di(phytosteryl/octyldodecyl) lauroyl glutamate, isopropyl lauroyl sarcosine, ethylhexyl methoxycinnamate and dicaprylyl carbonate; polyhydric alcohol fatty acid esters such as neopentyl glycol dicaprate, neopentyl glycol diethylhexanoate, glyceryl tri-2-ethylhexanoate (triethylhexanoin), glyceryl tri(caprylate/caprate), glyceryl tricaprylate, glyceryl tricaprate, trimethylolpropane triisostearate, pentaerythrityl tetraethylhexanoate, pentaerythrityl tetraisostearate, polyglyceryl-2 isostearate, polyglyceryl-2 diisostearate, polyglyceryl-2 triisostearate, polyglyceryl-2 tetraisostearate, diisostearyl malate, erythrityl triethylhexanoate, ditrimethylolpropane (isostearate/sebacate), ditrimethylolpropane triethylhexanoate, dipentaerythrityl tripolyhydroxystearate, trehalose isostearate esters, dipentaerythrityl pentaisostearate and ethylene glycol di-2-ethylhexanoate; vegetable oils such as avocado oil, camellia oil, turtle oil, macadamia nut oil, corn oil, sunflower oil, mink oil, olive oil, rapeseed oil, egg yolk oil, sesame oil, persic oil, wheat germ oil, sasanqua oil, castor oil, linseed oil, safflower oil, grapeseed oil, cottonseed oil, perilla oil, soybean oil, peanut oil, tea seed oil, torreya oil, rice bran oil, Chinese tung oil, Japanese tung oil, jojoba oil, germ oil, evening primrose oil, coconut oil and Argania spinosa kernel oil; linear polysiloxanes such as dimethylpolysiloxane (dimethicone), methylphenylpolysiloxane and methylhydrogenpolysiloxane; and cyclic polysiloxanes such as cyclopentasiloxane, octamethylcyclotetrasiloxane, decamethylcyclopentasiloxane, dodecamethylcyclohexasiloxane and tetrahydrotetramethylcyclotetrasiloxane. Among those described above, hydrogenated polydecene, mineral oil, squalane, triethylhexanoin, isononyl isononanoate, isopropyl myristate, glyceryl tri(caprylate/caprate), neopentyl glycol dicaprate, olive oil, macadamia nut oil, Argania spinosa kernel oil, castor oil, jojoba oil, dimethicone, methylphenylpolysiloxane, cyclopentasiloxane, dipentaerythrityl tripolyhydroxystearate, pentaerythrityl tetraethylhexanoate, diisostearyl malate, polyglyceryl-2 triisostearate, ethylhexyl hydroxystearate, di(phytosteryl/octyldodecyl) lauroyl glutamate, hydrogenated polyisobutene, cetyl ethylhexanoate and dipentaerythrityl tripolyhydroxystearate are preferred.

As the component (F) to be contained in the water-based cosmetic according to the present invention, at least one type of oil agent (an oil agent in a liquid form at 25° C.) can be used. That is, the component (F) may be a single type of oil agent (an oil agent in a liquid form at 25° C.), or two or more types of oil agents (oil agents in a liquid form at 25° C.) may be combined. When the water-based cosmetic according to the present invention contains an oil agent as the component (F), the content of the component (F) is preferably from 0.01 to 50% by mass and more preferably from 0.1 to 25% by mass, with respect to the total mass of the water-based cosmetic.

When the water-based cosmetic according to the present invention contains an oil agent in a paste form at 25° C. as the component (G), examples of the oil agent as the component (G) include vaseline, lanolin, purified lanolin, cholesteryl hydroxystearate, phytosteryl hydroxystearate, phytosteryl oleate, phytosteryl macadamiate, dipentaerythrityl hexa(hydroxystearate/stearate/rosinate), dipentaerythrityl hexahydroxystearate, dipentaerythrityl tetra(hydroxystearate/isostearate), glyceryl (ethylhexanoate/stearate/adipate), glyceryl tri(caprylate/caprate/myristate/stearate), di(phytosteryl/octyldodecyl/behenyl) lauroyl glutamate, (phytosteryl/isostearyl/cetyl/stearyl/behenyl) dimer dilinoleate, hydrogenated palm oil, hydrogenated coconut oil and hydrogenated castor oil. Among those described above, dipentaerythrityl hexa(hydroxystearate/stearate/rosinate), cholesteryl hydroxystearate, vaseline, lanolin, purified lanolin, phytosteryl oleate, dipentaerythrityl tetra(hydroxystearate/isostearate), dipentaerythrityl hexahydroxystearate, hydrogenated palm oil, hydrogenated coconut oil, hydrogenated castor oil, phytosteryl macadamiate, (phytosteryl/isostearyl/cetyl/stearyl/behenyl) dimer dilinoleate and di(phytosteryl/octyldodecyl/behenyl)lauroyl glutamate are preferable.

As the component (G) to be contained in the water-based cosmetic according to the present invention, at least one type of oil agent (an oil agent in a paste form at 25° C.) can be used. That is, the component (G) may be a single type of oil agent (an oil agent in a paste form at 25° C.), or two or more types of oil agents (oil agents in a paste form at 25° C.) may be combined. When the water-based cosmetic according to the present invention contains an oil agent as the component (G), the content of the component (G) is preferably from 0.01 to 10% by mass and more preferably from 0.1 to 5% by mass, with respect to the total mass of the water-based cosmetic.

When the water-based cosmetic according to the present invention contains an oil agent in a solid form at 25° C. as the component (H), examples of the oil agent as the component (H) include glyceryl (behenate/eicosadioate), glyceryl tri(behenate/isostearate/eicosadioate), polyglyceryl (behenate/eicosadioate), cetanol, stearyl alcohol, behenyl alcohol, microcrystalline wax, paraffin, polyethylene, candelilla wax, carnauba wax and bees wax. Among those described above, polyglyceryl (behenate/eicosadioate), glyceryl (behenate/isostearate/eicosadioate), cetanol, behenyl alcohol, microcrystalline wax and stearyl alcohol are preferable.

As the component (H) to be contained in the water-based cosmetic according to the present invention, at least one type of oil agent (an oil agent in a solid form at 25° C.) can be used. That is, the component (H) may be a single type of oil agent (an oil agent in a solid form at 25° C.), or two or more types of oil agents (oil agents in a solid form at 25° C.) may be combined. When the water-based cosmetic according to the present invention contains an oil agent as the component (H), the content of the component (H) is preferably from 0.01 to 10% by mass and more preferably from 0.1 to 5% by mass, with respect to the total mass of the water-based cosmetic.

To the water-based cosmetic according to the present invention, various components (hereinafter may be referred to as "other components") that do not correspond to the aforementioned components (A) to (H) and are generally used in cosmetics can be further added appropriately, if required, without impairing the effect of the present invention, for purposes such as improving the functionality, providing nutrients to the skin, and preventing quality degradation. More specifically, for example, water-soluble ionic substances, lower alcohols, monosaccharides, oligosaccharides, polysaccharides, amino acids, organic amines, preservatives, pH adjusting agents, vitamins, plant extracts, antioxidants, antioxidant assistants, ultraviolet absorbers, sequestering agents, fine particles, perfumes and the like can be mentioned. At least one (one or two or more) of these components can be used in combination.

The water-soluble ionic substance is one in which all or a portion thereof is dissociated into ions when dissolved in water, and inorganic salts, organic salts and the like are classified into this category. Examples of the inorganic salts include sodium chloride, potassium chloride, magnesium chloride, sodium sulfate, potassium sulfate and magnesium sulfate. Examples of the organic salts include citric acid, malic acid, tartaric acid and the salts thereof, ascorbic acid and the salts thereof, and ascorbic acid derivatives and the salts thereof.

Examples of the lower alcohols include alcohols having an alkyl group of 1 to 6 carbon atoms, and more specifically, methanol, ethanol, propanol, isopropanol, isobutyl alcohol, t-butyl alcohol and the like can be mentioned.

Examples of the monosaccharides include trioses such as D-glyceryl aldehyde and dihydroxyacetone; tetroses such as D-erythrose, D-erythrulose and D-threose; pentoses such as L-arabinose, D-xylose, L-lyxose, D-arabinose, D-ribose, D-ribulose, D-xylulose and L-xylulose; hexoses such as D-glucose, D-talose, D-psicose, D-galactose, D-fructose, L-galactose, L-mannose and D-tagatose; heptoses such as aldoheptose and heptulose; octoses such as octulose; deoxy sugars such as 2-deoxy-D-ribose, 6-deoxy-L-galactose and 6-deoxy-L-mannose; amino sugars such as D-glucosamine, D-galactosamine, sialic acid, aminouronic acid and muramic acid; and uronic acids such as D-glucuronic acid, D-mannuronic acid, L-guluronic acid, D-galacturonic acid and L-iduronic acid.

Examples of the oligosaccharides include sucrose, gentianose, umbelliferose, lactose, planteose, isolychnoses, α,α-trehalose, raffinose, lychnoses, umbilicin, stachyose and verbascoses.

Examples of the polysaccharides include cellulose, chondroitin sulfate, dextrin, glucomannan, chitin, galactan, dermatan sulfate, glycogen, gum arabic, heparan sulfate, gum tragacanth, keratan sulfate, chondroitin, mucoitin sulfate, guar gum, dextran, keratosulfate, locust bean gum, succinoglucan and colanic acid.

Examples of the amino acids include neutral amino acids such as threonine and cysteine, and basic amino acids such as hydroxylysine. In addition, as an amino acid derivative, for example, sodium acylsarcosine (sodium lauroylsarcosine), acyl glutamates, sodium acyl β-alanine, glutathione and the like can be mentioned.

Examples of the organic amines include monoethanolamine, diethanolamine, triethanolamine, morpholine, triisopropanolamine, 2-amino-2-methyl-1,3-propanediol and 2-amino-2-methyl-1-propanol.

Examples of the preservatives include methylparaben, ethylparaben, butylparaben and phenoxyethanol. The preservatives may be used alone, or two or more types thereof may be used in combination.

Examples of the pH adjusting agents include edetic acid, disodium edetate, citric acid, sodium citrate, sodium hydroxide, potassium hydroxide and triethanolamine. The pH adjusting agents may be used alone, or two or more types thereof may be used in combination.

Examples of the vitamins include vitamin A, vitamin B1, vitamin B2, vitamin B6, vitamin E, vitamin K and derivatives thereof, pantothenic acid and derivatives thereof, biotin and the like.

Examples of the plant extracts include aloe vera, witch hazel, hamamelis, cucumber, lemon, lavender and rose.

Examples of the antioxidants include oil-soluble vitamin C derivatives, tocopherols and derivatives thereof and salts thereof, dibutylhydroxytoluene, butylhydroxyanisole and gallic acid esters. The antioxidants may be used alone, or two or more types thereof may be used in combination.

Examples of the antioxidant assistants include phosphoric acid, citric acid, maleic acid, malonic acid, succinic acid, fumaric acid, cephalin, hexametaphosphate, phytic acid and ethylenediaminetetraacetic acid.

Examples of the ultraviolet absorbers include benzoic acid-based ultraviolet absorbers such as para-aminobenzoic acid (hereinafter sometimes abbreviated as PABA), PABA monoglycerin esters, N,N-dipropoxy PABA ethyl esters, N,N-diethoxy PABA ethyl esters, N,N-dimethyl PABA ethyl esters, N,N-dimethyl PABA butyl esters and N,N-dimethyl PABA ethyl esters; anthranilic acid-based ultraviolet absorbers such as homomenthyl-N-acetyl anthranilate; salicylic acid-based ultraviolet absorbers such as amyl salicylate, menthyl salicylate, homomenthyl salicylate, octyl salicylate, phenyl salicylate, benzyl salicylate and p-isopropanol phenyl salicylate; cinnamic acid-based ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, iso-amyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate and glyceryl mono-2-ethylhexanoyl-diparamethoxycinnamate; benzophenone-based ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxy-benzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; and 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazole, 2-(2'-hydroxy-5'-t-octylphenyl) benzotriazole, 2-(2'-hydroxy-5'-methylphenyl) benzotriazole, dibenzalazine, dianisoylmethane, 4-methoxy-4'-t-butyldibenzoylmethane, 5-(3,3-dimethyl-2-norbornylidene)-3-pentan-2-one and 2,4,6-trianilino-p-(carbo-2'-ethylhexyl-1'-oxy) 1,3,5-triazine and 4-tert-butyl-4'-methoxydibenzoylmethane. The ultraviolet absorbers may be used alone, or two or more types thereof may be used in combination.

Examples of the sequestering agents include disodium edetate, edetic acid salts, and hydroxyethane diphosphonic acid. The sequestering agents may be used alone, or two or more types thereof may be used in combination.

Examples of the fine particles include pigments such as inorganic pigments and organic pigments, and powder components such as talc.

Examples of the pigments include inorganic white pigments such as titanium dioxide and zinc oxide (also including fine particle types of titanium dioxide and zinc oxide that are used as ultraviolet scattering agents, or surface-coated inorganic white pigments whose surfaces are coated with fatty acid soaps such as aluminum stearate and zinc palmitate, fatty acids such as stearic acid, myristic acid and palmitic acid, fatty acid esters such as dextrin palmitate, and the like); inorganic red pigments such as iron oxide (red iron oxide) and iron titanate; inorganic brown pigments such as γ-iron oxide; inorganic yellow pigments such as yellow iron oxide and yellow ocher; inorganic black pigments such as black iron oxide, carbon black and lower titanium oxide; inorganic violet pigments such as mango violet and cobalt violet; inorganic green pigments such as chromium oxide, chromium hydroxide and cobalt titanate; inorganic blue pigments such as ultramarine blue and Prussian blue; pearl pigments such as titanium oxide-coated mica, titanium oxide-coated bismuth oxychloride, titanium oxide-coated talc, colored titanium oxide-coated mica, bismuth oxychloride and fish scale foil; metal powder pigments such as aluminum powder and copper powder; organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401 and Blue No. 404, and organic pigments of zirconium and barium or aluminum lake such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1. These pigments may be used alone, or two or more types thereof may be used in combination.

Examples of the powder components include inorganic powders such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstates, magnesium, silica, zeolite, barium sulfate, calcined calcium sulfate (calcined gypsum), calcium phosphate, fluoroapatite, hydroxyapatite, ceramic powder, metal soaps (zinc myristate, calcium palmitate, aluminum stearate) and boron nitride; and organic powders such as polyamide resin powders (nylon powders), polyethylene powders, polymethyl methacrylate powders, polystyrene powders, copolymer resin powders of styrene and acrylic acid, benzoguanamine resin powders, polytetrafluoroethylene powders and cellulose powders. The powder components may be used alone, or two or more types thereof may be used in combination.

In addition, those fine particles that have been subjected to a surface treatment may also be used. The surface treatment includes a hydrophobic treatment and a hydrophilic treatment. Examples of the hydrophobic treatment include a treatment with silicone compounds such as dimethylpolysiloxane, methylhydrogenpolysiloxane, trimethylsiloxysilicate, (alkyl acrylate/dimethicone) copolymers and (dimethicone/methicone) copolymers; a treatment with fluorine compounds such as fluorine-modified silicone, DEA perfluoroalkyl phosphate and perfluorooctyltriethoxysilane; a treatment with metal soaps such as zinc laurate, aluminum stearate and aluminum isostearate; a treatment with amino acids such as sodium lysine dilauroyl glutamate, lauroyl lysine, sodium lauroyl aspartate; a treatment with oils such as higher fatty acids, higher alcohols, esters and waxes; a treatment with polymers such as acrylate copolymers; and a treatment with silanes such as triethoxycaprylylsilane. Examples of the hydrophilic treatment include a treatment with metal oxides such as silica and alumina; a treatment with polysaccharides such as crystalline cellulose, cellulose, chitosan and sodium alginate; a treatment with sodium metaphosphate; and a treatment with methoxy PEG-10 propyltrimethoxysilane. In the present invention, the pigment added as the fine particles of the component (H) is preferably subjected to a surface treatment, more preferably subjected to a hydrophobic treatment, and most preferably subjected to a treatment with silicone.

The water-based cosmetic according to the present invention contains water. The content of water is preferably from 30 to 99% by mass, more preferably from 40 to 95% by mass, still more preferably from 50 to 92% by mass and particularly preferably from 50 to 85% by mass, with respect to the total mass of the water-based cosmetic.

It should be noted that the total mass of water and the components other than water in the water-based cosmetic is 100% by mass.

The water-based cosmetic according to the present invention can be applied not only to basic cosmetics such as cleansing lotions, cleansing gels, essences, skin lotions, milky lotions, creams and gels, but also to facial cleansers, hair styling agents and the like, and it can also be applied to make-up products such as eye shadows and foundations in which fine particles are dispersed in the water-based cosmetic. Further, the water-based cosmetic according to the present invention can also be made into basic cosmetics and make-up products stored in a wide mouth container.

In addition, these water-based cosmetics can be produced by a method for producing ordinary cosmetic preparations, and the production method thereof is not particularly limited.

As a method for producing the water-based cosmetic according to the present invention, for example, a method for producing a water-based cosmetic including:

a step of mixing, and heating and dissolving, the component (A), the component (B), the component (C), water and, if required, at least one component selected from the group consisting of the component (D), a surfactant and an oil agent (the component (F), the component (G) or the component (H)); and a step of stiffing and cooling the heated solution can be mentioned. It is preferable that the heating and dissolving processes are carried out at 85 to 100° C. and the stirring process is carried out with a homomixer, a propeller mixer or the like until a uniform solution is obtained. Further, it is more preferable to mix the component (A), the component (B) and water, and after heating and dissolving the resulting mixture at 85 to 100° C., mix other components. The cooling process is preferably carried out so as to cool to 25 to 40° C. by a conventional method.

One aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C)), preferably at least one selected from the group consisting of carboxyvinyl polymers, acrylic acid/alkyl methacrylate copolymers, acrylate copolymers, hydroxyethyl cellulose, hydroxypropyl methyl cellulose, polyvinyl alcohols, polyethylene glycol and sodium alginate, and more preferably at least one selected from the group consisting of carboxyvinyl polymers and acrylic acid/alkyl methacrylate copolymers;

and water, wherein, with respect to the total mass of the water-based cosmetic, the content of the component (A) is from 0.01 to 2% by mass, more preferably from 0.1 to 2% by mass, still more preferably from 0.1 to 1% by mass, and particularly preferably from 0.18 to 0.6% by mass, the content of the component (B) is from 0.01 to 2% by mass, more preferably from 0.1 to 2% by mass, still more preferably from 0.1 to 1% by mass, and particularly preferably from 0.12 to 0.4% by mass, the content of the component (C) is from 0.01 to 2% by mass, more preferably from 0.01 to 1% by mass, still more preferably from 0.05 to 0.5% by mass, and particularly preferably from 0.1 to 0.5% by mass, the content of water is from 30 to 99% by mass, preferably from 40 to 95% by mass, more preferably from 50 to 92% by mass, and particularly preferably from 50 to 85% by mass, the total content of the components (A) to (C) and the water does not exceed 100% by mass, the ratio of the content of the component (A) to the content of the component (B) is from 4:6 to 8:2 in mass ratio, more preferably from 4:6 to 7:3, still more preferably from 5:5 to 7:3, and particularly preferably from 6:4 to 7:3, and the ratio of the total content of the component (A) and the component (B) to the content of the component (C) is from 1:5 to 15:1 in mass ratio.

One aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of water is from 30 to 99% by mass, and the total content of the components (A) to (C) and the water does not exceed 100% by mass.

One aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of water is from 30 to 99% by mass, the total content of the components (A) to (C) and the water does not exceed 100% by mass, the ratio of the content of the component (A) to the content of the component (B) is from 6:4 to 7:3 in mass ratio, and the ratio of the total content of the component (A) and the component (B) to the content of the component (C) is from 1:5 to 15:1 in mass ratio.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C)), preferably at least one selected from the group consisting of carboxyvinyl polymers, acrylic acid/alkyl methacrylate copolymers, acrylate copolymers, hydroxyethyl cellulose, hydroxypropyl methyl cellulose, polyvinyl alcohols, polyethylene glycol and sodium alginate, and more preferably at least one selected from the group consisting of carboxyvinyl polymers and acrylic acid/alkyl methacrylate copolymers;

a moisturizing agent (component (D)), preferably at least one selected from the group consisting of glycerin, diglycerin, dipropylene glycol, 1,3-propanediol, PEG-20, sorbitol, trehalose, hyaluronic acid or a salt thereof, PPG-10 methyl glucose ether, polyoxyethylene methyl glucoside and erythritol; and water, wherein, with respect to the total mass of the water-based cosmetic, the content of the component (A) is from 0.01 to 2% by mass, more preferably from 0.1 to 2% by mass, still more preferably from 0.1 to 1% by mass, and particularly preferably from 0.18 to 0.6% by mass, the content of the component (B) is from 0.01 to 2% by mass, more preferably from 0.1 to 2% by mass, still more preferably from 0.1 to 1% by mass, and particularly preferably from 0.12 to 0.4% by mass, the content of the component (C) is from 0.01 to 2% by mass, more preferably from 0.01 to 1% by mass, still more preferably from 0.05 to 0.5% by mass, and particularly preferably from 0.1 to 0.5% by mass, the content of the component (D) is from 3 to 30% by mass and more preferably from 6 to 16.5% by mass, the content of water is from 30 to 99% by mass, preferably from 40 to 95% by mass, more preferably from 50 to 92% by mass, and particularly preferably from 50 to 85% by mass, the total content of the components (A) to (D) and the water does not exceed 100% by mass, the mass ratio between the content of the component (A) and the content of the component (B) is from 4:6 to 8:2, more preferably from 4:6 to 7:3, still more preferably from 5:5 to 7:3, and particularly preferably from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass, the content of water is from 50 to 92% by mass, and the total content of the components (A) to (D) and the water does not exceed 100% by mass.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass, the content of water is from 50 to 85% by mass, and the total content of the components (A) to (D) and the water does not exceed 100% by mass.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass, the content of water is from 50 to 92% by mass, the total content of the components (A) to (D) and the water does not exceed 100% by mass, the mass ratio between the content of the component (A) and the content of the component (B) is from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass, the content of water is from 50 to 85% by mass, the total content of the components (A) to (D) and the water does not exceed 100% by mass, the mass ratio between the content of the component (A) and the content of the component (B) is from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C)), preferably at least one selected from the group consisting of carboxyvinyl polymers, acrylic acid/alkyl methacrylate copolymers, acrylate copolymers, hydroxyethyl cellulose, hydroxypropyl methyl cellulose, polyvinyl alcohols, polyethylene glycol and sodium alginate, and more preferably at least one selected from the group consisting of carboxyvinyl polymers and acrylic acid/alkyl methacrylate copolymers;

a nonionic surfactant (component (E)), preferably at least one selected from the group consisting of POE-glycerin fatty acid esters, POE-hydrogenated castor oil, POE-alkyl ethers, POE-sorbitan fatty acid esters, cetearyl glucoside, modified silicone and polyglycerol fatty acid esters; and water, wherein, with respect to the total mass of the water-based cosmetic, the content of the component (A) is from 0.01 to 2% by mass, more preferably from 0.1 to 2% by mass, still more preferably from 0.1 to 1% by mass, and particularly preferably from 0.18 to 0.6% by mass, the content of the component (B) is from 0.01 to 2% by mass, more preferably from 0.1 to 2% by mass, still more preferably from 0.1 to 1% by mass, and particularly preferably from 0.12 to 0.4% by mass, the content of the component (C) is from 0.01 to 2% by mass, more preferably from 0.01 to 1% by mass, still more preferably from 0.05 to 0.5% by mass, and particularly preferably from 0.1 to 0.5% by mass, the content of the component (E) is from 0.01 to 40% by mass, more preferably from 0.01 to 20% by mass, and still more preferably from 0.01 to 10% by mass, the content of water is from 30 to 99% by mass, preferably from 40 to 95% by mass, more preferably from 50 to 92% by mass, and particularly preferably from 50 to 85% by mass, the total content of the components (A) to (C), the component (E) and the water does not exceed 100% by mass, the mass ratio between the content of the component (A) and the content of the component (B) is from 4:6 to 8:2, more preferably from 4:6 to 7:3, still more preferably from 5:5 to 7:3, and particularly preferably from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a nonionic surfactant (component (E)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (E) is from 0.01 to 10% by mass, the content of water is from 50 to 92% by mass, and the total content of the components (A) to (C), the component (E) and the water does not exceed 100% by mass.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a nonionic surfactant (component (E)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (E) is from 0.01 to 10% by mass, the content of water is from 50 to 92% by mass, the total content of the components (A) to (C), the component (E) and the water does not exceed 100% by mass, the mass ratio between the content of the component (A) and the content of the component (B) is from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C)), preferably at least one selected from the group consisting of carboxyvinyl polymers, acrylic acid/alkyl methacrylate copolymers, acrylate copolymers, hydroxyethyl cellulose, hydroxypropyl methyl cellulose, polyvinyl alcohols, polyethylene glycol and sodium alginate, and more preferably at least one selected from the group consisting of carboxyvinyl polymers and acrylic acid/alkyl methacrylate copolymers;

a moisturizing agent (component (D)), preferably at least one selected from the group consisting of glycerin, diglycerin, dipropylene glycol, 1,3-propanediol, PEG-20, sorbitol, trehalose, hyaluronic acid or a salt thereof, PPG-10 methyl glucose ether, polyoxyethylene methyl glucoside and erythritol; and at least one component selected from the group consisting of an oil agent in a liquid form at 25° C. (component (F)), an oil agent in a paste form at 25° C. (component (G)) and an oil agent in a solid form at 25° C. (component (H)); and water, wherein the aforementioned component (F) is preferably at least one selected from the group consisting of hydrogenated polydecene, mineral oil, squalane, triethylhexanoin, isononyl isononanoate, isopropyl myristate, glyceryl tri (caprylate/caprate), neopentyl glycol dicaprate, olive oil, macadamia nut oil, Argania spinosa kernel oil, castor oil, jojoba oil, dimethicone, methylphenylpolysiloxane, cyclopentasiloxane, dipentaerythrityl tripolyhydroxystearate, pentaerythrityl tetraethylhexanoate, diisostearyl malate, polyglyceryl-2 triisostearate, ethylhexyl hydroxystearate, di(phytosteryl/octyldodecyl) lauroyl glutamate, hydrogenated polyisobutene, cetyl ethylhexanoate and dipentaerythrityl tripolyhydroxystearate, the aforementioned component (G) is preferably at least one selected from the group consisting of dipentaerythrityl hexa(hydroxystearate/stearate/rosinate), cholesteryl hydroxystearate, vaseline, lanolin, purified lanolin, phytosteryl oleate, dipentaerythrityl tetra(hydroxystearate/isostearate), dipentaerythrityl hexahydroxystearate, hydrogenated palm oil, hydrogenated coconut oil, hydrogenated castor oil, phytosteryl macadamiate, (phytosteryl/isostearyl/cetyl/stearyl/behenyl) dimer dilinoleate and di(phytosteryl/octyldodecyl/behenyl) lauroyl glutamate, the aforementioned component (H) is preferably at least one component selected from the group consisting of polyglyceryl (behenate/eicosadioate), glyceryl (behenate/isostearate/eicosadioate), cetanol, behenyl alcohol, microcrystalline wax and stearyl alcohol, and, with respect to the total mass of the water-based cosmetic, the content of the component (A) is from 0.01 to 2% by mass, more preferably from 0.1 to 2% by mass, still more preferably from 0.1 to 1% by mass, and particularly preferably from 0.18 to 0.6% by mass, the content of the component (B) is from 0.01 to 2% by mass, more preferably from 0.1 to 2% by mass, still more preferably from 0.1 to 1% by mass, and particularly preferably from 0.12 to 0.4% by mass, the content of the component (C) is from 0.01 to 2% by mass, more preferably from 0.01 to 1% by mass, still more preferably from 0.05 to 0.5% by mass, and particularly preferably from 0.1 to 0.5% by mass, the content of the component (D) is from 3 to 30% by mass and more preferably from 6 to 16.5% by mass, the content of water is from 30 to 99% by mass, preferably from 40 to 95% by mass, more preferably from 50 to 92% by mass, and particularly preferably from 50 to 85% by mass, in the case of containing the component (F), the content of the component (F) is from 0.01 to 50% by mass and more preferably from 1 to 25% by mass, in the case of containing the component (G), the content of the component (G) is from 0.01 to 10% by mass and more preferably from 0.1 to 5% by mass, in the case of containing the component (H), the content of the component (H) is from 0.01 to 10% by mass and more preferably from 0.1 to 5% by mass, the total content of the components (A) to (D), the components (F) to (H) and the water does not exceed 100% by mass, the mass ratio between the content of the component (A) and the content of the component (B) is from 4:6 to 8:2, more preferably from 4:6 to 7:3, still more preferably from 5:5 to 7:3, and particularly preferably from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D)); at least one component selected from the group consisting of an oil agent in a liquid form at 25° C. (component (F)), an oil agent in a paste form at 25° C. (component (G)) and an oil agent in a solid form at 25° C. (component (H)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass, the content of water is from 50 to 92% by mass, in the case of containing the component (F), the content of the component (F) is from 1 to 25% by mass, in the case of containing the component (G), the content of the component (G) is from 0.1 to 5% by mass, in the case of containing the component (H), the content of the component (H) is from 0.1 to 5% by mass, and the total content of the components (A) to (D), the components (F) to (H) and the water does not exceed 100% by mass.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D));

at least one component selected from the group consisting of an oil agent in a liquid form at 25° C. (component (F)), an oil agent in a paste form at 25° C. (component (G)) and an oil agent in a solid form at 25° C. (component (H)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass, the content of water is from 50 to 85% by mass, in the case of containing the component (F), the content of the component (F) is from 1 to 25% by mass, in the case of containing the component (G), the content of the component (G) is from 0.1 to 5% by mass, in the case of containing the component (H), the content of the component (H) is from 0.1 to 5% by mass, and the total content of the components (A) to (D), the components (F) to (H) and the water does not exceed 100% by mass.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D));

at least one component selected from the group consisting of an oil agent in a liquid form at 25° C. (component (F)), an oil agent in a paste form at 25° C. (component (G)) and an oil agent in a solid form at 25° C. (component (H)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass, the content of water is from 50 to 92% by mass, in the case of containing the component (F), the content of the component (F) is from 1 to 25% by mass, in the case of containing the component (G), the content of the component (G) is from 0.1 to 5% by mass, in the case of containing the component (H), the content of the component (H) is from 0.1 to 5% by mass, the total content of the components (A) to (D), the components (F) to (H) and the water does not exceed 100% by mass, the mass ratio between the content of the component (A) and the content of the component (B) is from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D));

at least one component selected from the group consisting of an oil agent in a liquid form at 25° C. (component (F)), an oil agent in a paste form at 25° C. (component (G)) and an oil agent in a solid form at 25° C. (component (H)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass, the content of water is from 50 to 85% by mass, in the case of containing the component (F), the content of the component (F) is from 1 to 25% by mass, in the case of containing the component (0), the content of the component (G) is from 0.1 to 5% by mass, in the case of containing the component (H), the content of the component (H) is from 0.1 to 5% by mass, the total content of the components (A) to (D), the components (F) to (H) and the water does not exceed 100% by mass, the mass ratio between the content of the component (A) and the content of the component (B) is from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C)), preferably at least one selected from the group consisting of carboxyvinyl polymers, acrylic acid/alkyl methacrylate copolymers, acrylate copolymers, hydroxyethyl cellulose, hydroxypropyl methyl cellulose, polyvinyl alcohols, polyethylene glycol and sodium alginate, and more preferably at least one selected from the group consisting of carboxyvinyl polymers and acrylic acid/alkyl methacrylate copolymers;

a moisturizing agent (component (D)), preferably at least one selected from the group consisting of glycerin, diglycerin, dipropylene glycol, 1,3-propanediol, PEG-20, sorbitol, trehalose, hyaluronic acid or a salt thereof, PPG-10 methyl glucose ether, polyoxyethylene methyl glucoside and erythritol;

a nonionic surfactant (component (E)), preferably at least one selected from the group consisting of POE-glycerin fatty acid esters, POE-hydrogenated castor oil, POE-alkyl ethers, POE-sorbitan fatty acid esters, cetearyl glucoside, modified silicone and polyglycerol fatty acid esters; and
water,
wherein, with respect to the total mass of the water-based cosmetic,
the content of the component (A) is from 0.01 to 2% by mass, more preferably from 0.1 to 2% by mass, still more preferably from 0.1 to 1% by mass, and particularly preferably from 0.18 to 0.6% by mass,
the content of the component (B) is from 0.01 to 2% by mass, more preferably from 0.1 to 2% by mass, still more preferably from 0.1 to 1% by mass, and particularly preferably from 0.12 to 0.4% by mass,
the content of the component (C) is from 0.01 to 2% by mass, more preferably from 0.01 to 1% by mass, still more preferably from 0.05 to 0.5% by mass, and particularly preferably from 0.1 to 0.5% by mass,
the content of the component (D) is from 3 to 30% by mass and more preferably from 6 to 16.5% by mass,
the content of the component (E) is from 0.01 to 40% by mass, more preferably from 0.01 to 20% by mass, and still more preferably from 0.01 to 10% by mass,
the content of water is from 30 to 99% by mass, preferably from 40 to 95% by mass, more preferably from 50 to 92% by mass, and particularly preferably from 50 to 85% by mass,
the total content of the components (A) to (E) and the water does not exceed 100% by mass,
the mass ratio between the content of the component (A) and the content of the component (B) is from 4:6 to 8:2, more preferably from 4:6 to 7:3, still more preferably from 5:5 to 7:3, and particularly preferably from 6:4 to 7:3, and
the mass ratio between the total content of the components (A) and (B) and the content of the component (C) is from 1:5 to 15:1.
Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of water is from 50 to 92% by mass, and
the total content of the components (A) to (E) and the water does not exceed 100% by mass.
Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of water is from 50 to 85% by mass, and
the total content of the components (A) to (E) and the water does not exceed 100% by mass.
Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of water is from 50 to 92% by mass,
the total content of the components (A) to (E) and the water does not exceed 100% by mass,
the mass ratio between the content of the component (A) and the content of the component (B) is from 6:4 to 7:3, and
the mass ratio between the total content of the components (A) and (B) and the content of the component (C) is from 1:5 to 15:1.
Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass, the content of the component (D) is from 6 to 16.5% by mass, the content of the component (E) is from 0.01 to 10% by mass, the content of water is from 50 to 85% by mass, the total content of the components (A) to (E) and the water does not exceed 100% by mass, the mass ratio between the content of the component (A) and the content of the component (B) is from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C)), preferably at least one selected from the group consisting of carboxyvinyl polymers, acrylic acid/alkyl methacrylate copolymers, acrylate copolymers, hydroxyethyl cellulose, hydroxypropyl methyl cellulose, polyvinyl alcohols, polyethylene glycol and sodium alginate, and more preferably at least one selected from the group consisting of carboxyvinyl polymers and acrylic acid/alkyl methacrylate copolymers;

a moisturizing agent (component (D)), preferably at least one selected from the group consisting of glycerin, diglycerin, dipropylene glycol, 1,3-propanediol, PEG-20, sorbitol, trehalose, hyaluronic acid or a salt thereof, PPG-10 methyl glucose ether, polyoxyethylene methyl glucoside and erythritol;

a nonionic surfactant (component (E)), preferably at least one selected from the group consisting of POE-glycerin fatty acid esters, POE-hydrogenated castor oil, POE-alkyl ethers, POE-sorbitan fatty acid esters, cetearyl glucoside, modified silicone and polyglycerol fatty acid esters;

at least one component selected from the group consisting of an oil agent in a liquid form at 25° C. (component (F)), an oil agent in a paste form at 25° C. (component (G)) and an oil agent in a solid form at 25° C. (component (H)); and water, wherein the aforementioned component (F) is preferably at least one selected from the group consisting of hydrogenated polydecene, mineral oil, squalane, triethylhexanoin, isononyl isononanoate, isopropyl myristate, glyceryl tri (caprylate/caprate), neopentyl glycol dicaprate, olive oil, macadamia nut oil, Argania spinosa kernel oil, castor oil, jojoba oil, dimethicone, methylphenylpolysiloxane, cyclopentasiloxane, dipentaerythrityl tripolyhydroxystearate, pentaerythrityl tetraethylhexanoate, diisostearyl malate, polyglyceryl-2 triisostearate, ethylhexyl hydroxystearate, di(phytosteryl/octyldodecyl) lauroyl glutamate, hydrogenated polyisobutene, cetyl ethylhexanoate and dipentaerythrityl tripolyhydroxystearate, the aforementioned component (G) is preferably at least one selected from the group consisting of dipentaerythrityl hexa(hydroxystearate/stearate/rosinate), cholesteryl hydroxystearate, vaseline, lanolin, purified lanolin, phytosteryl oleate, dipentaerythrityl tetra(hydroxystearate/isostearate), dipentaerythrityl hexahydroxystearate, hydrogenated palm oil, hydrogenated coconut oil, hydrogenated castor oil, phytosteryl macadamiate, (phytosteryl/isostearyl/cetyl/stearyl/behenyl) dimer dilinoleate and di(phytosteryl/octyldodecyl/behenyl) lauroyl glutamate, the aforementioned component (H) is preferably at least one component selected from the group consisting of polyglyceryl (behenate/eicosadioate), glyceryl (behenate/isostearate/eicosadioate), cetanol, behenyl alcohol, microcrystalline wax and stearyl alcohol, and, with respect to the total mass of the water-based cosmetic, the content of the component (A) is from 0.01 to 2% by mass, more preferably from 0.1 to 2% by mass, still more preferably from 0.1 to 1% by mass, and particularly preferably from 0.18 to 0.6% by mass, the content of the component (B) is from 0.01 to 2% by mass, more preferably from 0.1 to 2% by mass, still more preferably from 0.1 to 1% by mass, and particularly preferably from 0.12 to 0.4% by mass, the content of the component (C) is from 0.01 to 2% by mass, more preferably from 0.01 to 1% by mass, still more preferably from 0.05 to 0.5% by mass, and particularly preferably from 0.1 to 0.5% by mass, the content of the component (D) is from 3 to 30% by mass and more preferably from 6 to 16.5% by mass, the content of the component (E) is from 0.01 to 40% by mass, more preferably from 0.01 to 20% by mass, and still more preferably from 0.01 to 10% by mass, the content of water is preferably from 30 to 99% by mass, more preferably from 40 to 95% by mass, still more preferably from 50 to 92% by mass, and particularly preferably from 50 to 85% by mass, in the case of containing the component (F), the content of the component (F) is from 0.01 to 50% by mass and more preferably from 1 to 25% by mass, in the case of containing the component (G), the content of the component (G) is from 0.01 to 10% by mass and more preferably from 0.1 to 5% by mass, in the case of containing the component (H), the content of the component (H) is from 0.01 to 10% by mass and more preferably from 0.1 to 5% by mass, the total content of the components (A) to (H) and the water does not exceed 100% by mass, the mass ratio between the content of the component (A) and the content of the component (B) is from 4:6 to 8:2, more preferably from 4:6 to 7:3, still more preferably from 5:5 to 7:3, and particularly preferably from 6:4 to 7:3, and the mass ratio between the total content of the components (A) and (B) and the content of the component (C) is from 1:5 to 15:1.

Another aspect of the water-based cosmetic of the present invention is a water-based cosmetic containing:

agar having a weight average molecular weight of 10,000 to 60,000 (component (A));

xanthan gum (component (B));

a water-soluble polymer (excluding the components (A) and (B)) (component (C));

a moisturizing agent (component (D));

a nonionic surfactant (component (E));

at least one component selected from the group consisting of an oil agent in a liquid form at 25° C. (component (F)), an oil agent in a paste form at 25° C. (component (G)) and an oil agent in a solid form at 25° C. (component (H)); and water, wherein, with respect to the total mass of the water-based cosmetic, the content of the component (A) is from 0.18 to 0.6% by mass, the content of the component (B) is from 0.12 to 0.4% by mass, the content of the component (C) is from 0.1 to 0.5% by mass, the content of the component (D) is from 6 to 16.5% by mass,
the content of the component (E) is from 0.01 to 10% by mass,
the content of water is from 50 to 92% by mass,
in the case of containing the component (F), the content of the component (F) is from 1 to 25% by mass,
in the case of containing the component (G), the content of the component (G) is from 0.1 to 5% by mass,
in the case of containing the component (H), the content of the component (H) is from 0.1 to 5% by mass, and
the total content of the components (A) to (H) and the water does not exceed 100% by mass.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
at least one component selected from the group consisting of an oil agent in a liquid form at 25° C. (component (F)), an oil agent in a paste form at 25° C. (component (G)) and an oil agent in a solid form at 25° C. (component (H)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of water is from 50 to 85% by mass,
in the case of containing the component (F), the content of the component (F) is from 1 to 25% by mass,
in the case of containing the component (G), the content of the component (G) is from 0.1 to 5% by mass,
in the case of containing the component (H), the content of the component (H) is from 0.1 to 5% by mass, and
the total content of the components (A) to (H) and the water does not exceed 100% by mass.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
at least one component selected from the group consisting of an oil agent in a liquid form at 25° C. (component (F)), an oil agent in a paste form at 25° C. (component (G)) and an oil agent in a solid form at 25° C. (component (H)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of water is from 50 to 92% by mass,
in the case of containing the component (F), the content of the component (F) is from 1 to 25% by mass,
in the case of containing the component (G), the content of the component (G) is from 0.1 to 5% by mass,
in the case of containing the component (H), the content of the component (H) is from 0.1 to 5% by mass,
the total content of the components (A) to (H) and the water does not exceed 100% by mass,
the mass ratio between the content of the component (A) and the content of the component (B) is from 6:4 to 7:3, and
the mass ratio between the total content of the components (A) and (B) and the content of the component (C) is from 1:5 to 15:1.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
at least one component selected from the group consisting of an oil agent in a liquid form at 25° C. (component (F)), an oil agent in a paste form at 25° C. (component (G)) and an oil agent in a solid form at 25° C. (component (F1)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of water is from 50 to 85% by mass,
in the case of containing the component (F), the content of the component (F) is from 1 to 25% by mass,
in the case of containing the component (G), the content of the component (G) is from 0.1 to 5% by mass,
in the case of containing the component (H), the content of the component (H) is from 0.1 to 5% by mass,
the total content of the components (A) to (H) and the water does not exceed 100% by mass,
the mass ratio between the content of the component (A) and the content of the component (B) is from 6:4 to 7:3, and
the mass ratio between the total content of the components (A) and (B) and the content of the component (C) is from 1:5 to 15:1.

Another aspect of the water-based cosmetic of the present invention is a water-based cosmetic containing:
agar having a weight average molecular weight of 10,000 to 60,000 (component (A));
xanthan gum (component (B));

a water-soluble polymer (excluding the components (A) and (B)) (component (C));
a moisturizing agent (component (D));
a nonionic surfactant (component (E));
an oil agent in a liquid form at 25° C. (component (F)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of the component (F) is from 1 to 25% by mass,
the content of water is from 50 to 92% by mass, and
the total content of the components (A) to (F) and the water does not exceed 100% by mass.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
an oil agent in a liquid form at 25° C. (component (F)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of the component (F) is from 1 to 25% by mass,
the content of water is from 50 to 85% by mass, and
the total content of the components (A) to (F) and the water does not exceed 100% by mass.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
an oil agent in a liquid form at 25° C. (component (F)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of the component (F) is from 1 to 25% by mass,
the content of water is from 50 to 92% by mass,
the total content of the components (A) to (F) and the water does not exceed 100% by mass,
the mass ratio between the content of the component (A) and the content of the component (B) is from 6:4 to 7:3, and
the mass ratio between the total content of the components (A) and (B) and the content of the component (C) is from 1:5 to 15:1.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
an oil agent in a liquid form at 25° C. (component (F)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass, the content of the component (F) is from 1 to 25% by mass,
the content of water is from 50 to 85% by mass,
the total content of the components (A) to (F) and the water does not exceed 100% by mass,
the mass ratio between the content of the component (A) and the content of the component (B) is from 6:4 to 7:3, and
the mass ratio between the total content of the components (A) and (B) and the content of the component (C) is from 1:5 to 15:1.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
an oil agent in a liquid form at 25° C. (component (F));
an oil agent in a paste form at 25° C. (component (G));
an oil agent in a solid form at 25° C. (component (H)); and
water, wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
in the case of containing the component (F), the content of the component (F) is from 1 to 25% by mass,
in the case of containing the component (G), the content of the component (G) is from 0.1 to 5% by mass,
in the case of containing the component (H), the content of the component (H) is from 0.1 to 5% by mass,
the content of water is from 50 to 92% by mass, and
the total content of the components (A) to (H) and the water does not exceed 100% by mass.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
an oil agent in a liquid form at 25° C. (component (F));
an oil agent in a paste form at 25° C. (component (G));
an oil agent in a solid form at 25° C. (component (H)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
in the case of containing the component (F), the content of the component (F) is from 1 to 25% by mass,
in the case of containing the component (G), the content of the component (G) is from 0.1 to 5% by mass,
in the case of containing the component (H), the content of the component (H) is from 0.1 to 5% by mass,
the content of water is from 50 to 85% by mass, and
the total content of the components (A) to (H) and the water does not exceed 100% by mass.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
an oil agent in a liquid form at 25° C. (component (F));
an oil agent in a paste form at 25° C. (component (G));
an oil agent in a solid form at 25° C. (component (H)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of the component (F) is from 1 to 25% by mass,
the content of the component (G) is from 0.1 to 5% by mass,
the content of the component (H) is from 0.1 to 5% by mass,
the content of water is from 50 to 92% by mass,
the total content of the components (A) to (H) and the water does not exceed 100% by mass,
the mass ratio between the content of the component (A) and the content of the component (B) is from 6:4 to 7:3, and
the mass ratio between the total content of the components (A) and (B) and the content of the component (C) is from 1:5 to 15:1.

Another aspect of the water-based cosmetic of the present invention is a water-based cosmetic containing:
agar having a weight average molecular weight of 10,000 to 60,000 (component (A));
xanthan gum (component (B));
a water-soluble polymer (excluding the components (A) and (B)) (component (C));
a moisturizing agent (component (D));
a nonionic surfactant (component (E));
an oil agent in a liquid form at 25° C. (component (F));
an oil agent in a paste form at 25° C. (component (G));
an oil agent in a solid form at 25° C. (component (H)); and
water,
wherein, with respect to the total mass of the water-based cosmetic,
the content of the component (A) is from 0.18 to 0.6% by mass,
the content of the component (B) is from 0.12 to 0.4% by mass,
the content of the component (C) is from 0.1 to 0.5% by mass,
the content of the component (D) is from 6 to 16.5% by mass,
the content of the component (E) is from 0.01 to 10% by mass,
the content of the component (F) is from 1 to 25% by mass,
the content of the component (G) is from 0.1 to 5% by mass,
the content of the component (H) is from 0.1 to 5% by mass,
the content of water is from 50 to 85% by mass,
the total content of the components (A) to (H) and the water does not exceed 100% by mass,
the mass ratio between the content of the component (A) and the content of the component (B) is from 6:4 to 7:3, and
the mass ratio between the total content of the components (A) and (B) and the content of the component (C) is from 1:5 to 15:1.

EXAMPLES

Hereinafter, the present invention will be described in more detail with reference to examples of the present invention and comparative examples, although the present invention is not limited thereto.

In the following Examples, "Ena" (manufactured by Ina Food Industry Co., Ltd., weight average molecular weight: 43,000, number average molecular weight: 8,800, Mw/Mn: 4.9) and "Agar S-7" (manufactured by Ina Food Industry Co., Ltd., weight average molecular weight: 290,000, number average molecular weight: 48,000, Mw/Mn: 6.0) were used as low molecular weight agar of the component (A) and high molecular weight agar, respectively.

Examples 1 to 10, Comparative Examples 1 to 6

In the formulations shown in Tables 1 and 2, all components were weighed in a beaker, mixed, heated to 85 to 95° C. to dissolve, and then cooled with stirring. A gel essence obtained as a result of degassing under reduced pressure was used as a sample.

TABLE 1

(% by mass)

| | | Examples | | | | | | | | | |
|---|---|---|---|---|---|---|---|---|---|---|---|
| | | 1 | 2 | 3 | 4 | 5 | 6 | 7 | 8 | 9 | 10 |
| A | Low molecular weight agar | 0.35 | 0.30 | 0.24 | 0.24 | 0.24 | 0.24 | 0.24 | 0.24 | 0.24 | 0.24 |
| | High molecular weight agar | — | — | — | — | — | — | — | — | — | — |
| B | Xanthan gum *1 | 0.15 | 0.20 | 0.16 | 0.16 | 0.16 | 0.16 | 0.16 | 0.16 | 0.16 | 0.16 |
| C | Carboxyvinyl polymer *2 | 0.50 | 0.50 | 0.50 | — | — | — | — | — | — | — |
| C | Acrylic acid/alkyl methacrylate copolymer *3 | — | — | — | 0.50 | — | — | — | — | — | — |
| C | Hydroxyethyl cellulose *4 | — | — | — | — | 0.50 | — | — | — | — | — |
| C | Hydroxypropyl methyl cellulose *5 | — | — | — | — | — | 0.50 | — | — | — | — |
| C | Polyvinyl alcohol *6 | — | — | — | — | — | — | 0.50 | — | — | — |
| C | Acrylate copolymer *7 | — | — | — | — | — | — | — | 0.50 | — | — |
| C | PEG-90 M *8 | — | — | — | — | — | — | — | — | 0.50 | — |
| C | Sodium alginate *9 | — | — | — | — | — | — | — | — | — | 0.50 |
| | Sodium hydroxide | Appropriate amount | Appropriate amount | Appropriate amount | Appropriate amount | Appropriate amount | Appropriate amount | Appropriate amount | Appropriate amount | Appropriate amount | Appropriate amount |
| | Water | Balance | Balance | Balance | Balance | Balance | Balance | Balance | Balance | Balance | Balance |
| Total | | 100 | 100 | 100 | 100 | 100 | 100 | 100 | 100 | 100 | 100 |

*1 "NOMCORT ZZ" (manufactured by The Nisshin OilliO Group, Ltd.)
*2 "Carbopol 980" (manufactured by Lubrizol Japan Limited)
*3 "Pemulen TR-1" (manufactured by Lubrizol Japan Limited)
*4 "Natrosol HEC" (manufactured by Ashland Inc.)
*5 "Metolose 65SH-4000" (manufactured by Shin-Etsu Chemical Co., Ltd.)
*6 "Kuraray Poval 235" (manufactured by Kuraray Co., Ltd.)
*7 "Carbopol AQUA SF-1 Polymer" (manufactured by Lubrizol Japan Limited)
*8 "Alkox E-160G" (manufactured by Meisei Chemical Works, Ltd.)
*9 "ADS-Oligonol" (manufactured by Ichimaru Pharcos Co., Ltd.)

TABLE 2

(% by mass)

| | | Comparative Examples | | | | | |
|---|---|---|---|---|---|---|---|
| | | 1 | 2 | 3 | 4 | 5 | 6 |
| A | Low molecular weight agar | 0.40 | — | — | — | — | — |
| | High molecular weight agar | — | 0.40 | — | — | — | — |
| B | Xanthan gum *1 | — | — | 0.40 | 0.50 | — | — |
| C | Carboxyvinyl polymer *2 | 0.50 | 0.50 | 0.50 | 0.50 | 0.50 | 1.00 |
| | Sodium hydroxide | Appropriate amount | Appropriate amount | Appropriate amount | Appropriate amount | Appropriate amount | Appropriate amount |
| | Water | Balance | Balance | Balance | Balance | Balance | Balance |
| Total | | 100 | 100 | 100 | 100 | 100 | 100 |

*1 "NOMCORT ZZ" (manufactured by The Nisshin OilliO Group, Ltd.)
*2 "Carbopol 980" (manufactured by Lubrizol Japan Limited)

(Impression of Usability)

Samples of Examples 1 to 3 and Comparative Examples 1 to 6 were applied to the entire face of 15 panelists, after washing the face, who were asked to answer the questionnaire regarding their impressions of usability of these samples, and the "ease of scooping (scoopability) with a finger", "feeling of compatibility, as if to blend in, with the skin (skin compatibility)", "sliminess", "stickiness", "freshness" and "moist feeling" were evaluated in accordance with the following criteria.

"Scoopability with a Finger"

a: 12 or more panelists answered that it was easy to scoop with a finger.

b: 8 to 11 panelists answered that it was easy to scoop with a finger.

c: 4 to 7 panelists answered that it was easy to scoop with a finger.

d: 3 or less panelists answered that it was easy to scoop with a finger.

"Skin Compatibility"

a: 12 or more panelists answered that there was a feeling of compatibility, as if to blend in, with the skin.

b: 8 to 11 panelists answered that there was a feeling of compatibility, as if to blend in, with the skin.

c: 4 to 7 panelists answered that there was a feeling of compatibility, as if to blend in, with the skin.

d: 3 or less panelists answered that there was a feeling of compatibility, as if to blend in, with the skin.

"Sliminess"

a: 12 or more panelists answered that there was no sliminess.

b: 8 to 11 panelists answered that there was no sliminess.

c: 4 to 7 panelists answered that there was no sliminess.

d: 3 or less panelists answered that there was no sliminess.

"Stickiness"

a: 12 or more panelists answered that there was no stickiness.

b: 8 to 11 panelists answered that there was no stickiness.

c: 4 to 7 panelists answered that there was no stickiness.

d: 3 or less panelists answered that there was no stickiness.

"Freshness"

a: 12 or more panelists answered that there was a feeling of freshness.

b: 8 to 11 panelists answered that there was a feeling of freshness.

c: 4 to 11 panelists answered that there was a feeling of freshness.

d: 3 or less panelists answered that there was a feeling of freshness.

"Moist Feeling"

a: 12 or more panelists answered that there was a moist feeling.

b: 8 to 11 panelists answered that there was a moist feeling.

c: 4 to 7 panelists answered that there was a moist feeling.

d: 3 or less panelists answered that there was a moist feeling.

TABLE 3

|  | Examples | | | Comparative Examples | | | | | |
|---|---|---|---|---|---|---|---|---|---|
|  | 1 | 2 | 3 | 1 | 2 | 3 | 4 | 5 | 6 |
| Scoopability with a finger | a | a | a | b | b | d | d | d | b |
| Skin compatibility | b | b | b | b | c | c | c | d | d |
| Sliminess | a | a | a | b | b | d | d | a | a |
| Stickiness | a | a | a | b | c | d | d | c | c |
| Freshness | a | a | a | d | d | c | c | a | b |
| Moist feeling | b | b | b | c | c | c | c | d | d |

The evaluation results are shown in Table 3. As a result, the gel essences of Examples 1 to 3 containing low molecular weight agar as the component (A), xanthan gum as the component (B) and a water-soluble polymer as the component (C) had no sliminess and stickiness, and exhibited favorable scoopability with a finger, skin compatibility, feeling of freshness and moist feeling. On the other hand, the gel essences of Comparative Examples 3 to 5 that did not contain at least one of agar and xanthan gum as the component (B) easily dripped off when scooped with a finger, and exhibited poor scoopability (that is, ease of scooping with a finger). Further, the gel essences of Comparative Examples 5 and 6 that did not contain the xanthan gum as the component (B) exhibited poor skin compatibility (that is, poor compatibility, as if to blend in, with the skin) and also lacked a moist feeling, although there was no sliminess.

Examples 11 to 15, Comparative Examples 7 to 9

In the formulations shown in Table 4, all components were weighed in a beaker, mixed, heated to 85 to 95° C. to dissolve, and then cooled with stirring. A water-based essence obtained as a result of degassing under reduced pressure was used as a sample. The same low molecular weight agar, xanthan gum, and carboxyvinyl polymer as those in Example 1 were used.

TABLE 4

(% by mass)

| | | | Examples | | | | | Comparative Examples | | |
|---|---|---|---|---|---|---|---|---|---|---|
| | | | 11 | 12 | 13 | 14 | 15 | 7 | 8 | 9 |
| A | Low molecular weight agar | | 0.60 | 0.60 | 0.60 | 0.60 | 0.60 | 0.60 | — | — |
| B | Xanthan gum | | 0.40 | 0.40 | 0.40 | 0.40 | 0.40 | 0.40 | — | — |
| C | Carboxyvinyl polymer | | 0.10 | 0.10 | 0.10 | 0.10 | 0.10 | — | 0.10 | 0.20 |
| | Methylparaben | | 0.10 | 0.10 | 0.10 | 0.10 | 0.10 | 0.10 | 0.10 | 0.10 |
| | Propylparaben | | 0.05 | 0.05 | 0.05 | 0.05 | 0.05 | 0.05 | 0.05 | 0.05 |
| D | Glycerin *1 | | 5.00 | 5.00 | 5.00 | 5.00 | 5.00 | 5.00 | 5.00 | 5.00 |
| D | Dipropylene glycol *2 | | 1.00 | 1.00 | 1.00 | 1.00 | 1.00 | 1.00 | 1.00 | 1.00 |
| E | PEG-20 glyceryl triisostearate *3 | | 1.00 | — | — | — | — | 1.00 | 1.00 | 1.00 |

TABLE 4-continued

| | | Examples | | | | | Comparative Examples (% by mass) | | |
|---|---|---|---|---|---|---|---|---|---|
| | | 11 | 12 | 13 | 14 | 15 | 7 | 8 | 9 |
| E | PEG-40 hydrogenated castor oil *4 | — | 1.00 | — | — | — | — | — | — |
| E | Laureth-7 *5 | — | — | 1.00 | — | — | — | — | — |
| E | Polysorbate 60 *6 | — | — | — | 1.00 | — | — | — | — |
| E | PEG-20 sorbitan cocoate *7 | — | — | — | — | 1.00 | — | — | — |
| | Citric acid | 0.01 | 0.01 | 0.01 | 0.01 | 0.01 | 0.01 | 0.01 | 0.01 |
| | Sodium citrate *8 | 0.09 | 0.09 | 0.09 | 0.09 | 0.09 | 0.09 | 0.09 | 0.09 |
| | Sodium hydroxide | 0.03 | 0.03 | 0.03 | 0.03 | 0.03 | — | 0.03 | 0.06 |
| | Water | 91.62 | 91.62 | 91.62 | 91.62 | 91.62 | 91.75 | 92.62 | 92.49 |
| Total | | 100 | 100 | 100 | 100 | 100 | 100 | 100 | 100 |

*1 "Concentrated glycerin for cosmetics" (manufactured by Sakamoto Yakuhin Kogyo Co., Ltd.)
*2 "DPG-RF" (manufactured by Adeka Corporation)
*3 "SALACOS GE-318" (manufactured by The Nisshin OilliO Group, Ltd.)
*4 "EMANON CH-40" (manufactured by Kao Corporation)
*5 "EMULMIN NL-70" (manufactured by Sanyo Chemical Industries, Ltd.)
*6 "RHEODOL TW-S120V" (manufactured by Kao Corporation)
*7 "EMALEX ET-2020" (manufactured by Nihon Emulsion Co., Ltd.)

(Impression of Usability)

The "ease of scooping (scoopability) with a finger", "feeling of compatibility, as if to blend in, with the skin (skin compatibility)", "sliminess", "stickiness", "freshness" and "moist feeling" of the samples of Example 11 and Comparative Examples 7 to 9 were evaluated in the same manner as in Example 1.

TABLE 5

| | Example | Comparative Examples | | |
|---|---|---|---|---|
| | 11 | 7 | 8 | 9 |
| Scoopability with a finger | a | a | d | c |
| Skin compatibility | a | b | d | d |
| Sliminess | a | c | b | b |
| Stickiness | a | d | c | c |
| Freshness | a | c | a | b |
| Moist feeling | b | b | d | d |

The evaluation results are shown in Table 5. As a result, the water-based essence of Example 11 containing low molecular weight agar as the component (A), xanthan gum as the component (B) and a water-soluble polymer as the component (C) had no sliminess and stickiness, and exhibited favorable scoopability with a finger, skin compatibility, feeling of freshness and moist feeling. On the other hand, the water-based essence of Comparative Example 7 that did not contain a water-soluble polymer as the component (C) had stickiness and sliminess, although the scoopability with a finger was favorable, and the water-based essences of Comparative Examples 8 and 9 that did not contain low molecular weight agar as the component (A) and xanthan gum as the component (B) were both evaluated as poor in terms of scoopability with a finger, skin compatibility and moist feeling.

Examples 16 to 25, Comparative Examples 10 to 11

In the formulations shown in Tables 6 and 7, all components were weighed in a beaker, mixed, heated to 85 to 95° C. to dissolve, and then cooled with stirring. An oil-in-water emulsion type essence obtained as a result of degassing under reduced pressure was used as a sample. The same low molecular weight agar, xanthan gum and carboxyvinyl polymer as those used in Example 1 and the same glycerin as that used in Example 11 were used, respectively.

TABLE 6

| | | Examples | Comparative Examples | |
|---|---|---|---|---|
| | | 16 to 25 | 10 | 11 |
| A | Low molecular weight agar | 0.3 | — | 0.6 |
| B | Xanthan gum | 0.2 | — | 0.4 |
| C | Carboxyvinyl polymer | 0.1 | 0.2 | — |
| D | Refer to Table 7 | 6 | 6 | 6 |
| E | Polyglyceryl-10 oleate*1 | 0.5 | 0.5 | 0.5 |
| F1 | Refer to Table 7 | 0.35 | 0.35 | 0.35 |
| F2 | Refer to Table 7 | 0.6 | 0.6 | 0.6 |
| F3 | Refer to Table 7 | 0.85 | 0.85 | 0.85 |
| G | Dipentaerythrityl hexa(hydroxystearate/stearate/rosinate)*2 | 0.25 | 0.25 | 0.25 |
| G | Cholesteryl hydroxystearate*3 | 0.15 | 0.15 | 0.15 |
| H | Refer to Table 7 | 0.3 | 0.3 | 0.3 |
| | Sodium hydroxide | 0.036 | 0.073 | — |
| | 1,2-pentanediol | 3.5 | 3.5 | 3.5 |
| | Phenoxyethanol | 0.2 | 0.2 | 0.2 |
| | Methylparaben | 0.1 | 0.1 | 0.1 |
| | Butylparaben | 0.05 | 0.05 | 0.05 |
| | EDTA-2Na | 0.005 | 0.005 | 0.005 |
| | (Vinyl dimethicone/methicone silsesquioxane) crosspolymer | 2.5 | 2.5 | 2.5 |
| | Hydrogenated lecithin | 0.2 | 0.2 | 0.2 |
| | Water | 83.809 | 84.172 | 83.445 |
| Total | | 100 | 100 | 100 |

*1 "SALACOS PG-180" (manufactured by The Nisshin OilliO Group, Ltd.)
*2 "COSMOL 168ARV" (manufactured by The Nisshin OilliO Group, Ltd.)
*3 "SALACOS HS" (manufactured by The Nisshin OilliO Group, Ltd.)

TABLE 7

| | D | F1 | F2 | F3 | H |
|---|---|---|---|---|---|
| Example 16 | Glycerin | Hydrogenated polydecene*16 | Triethylhexanoin*12 | Dimethicone*20 | Glyceryl (behenate/isostearate/eicosadioate)*23 |
| Example 17 | Polyglycerol*1 | Mineral oil*11 | Isononyl isononanoate*13 | Methylphenyl polysiloxane*21 | Glyceryl (behenate/isostearate/eicosadioate)*23 |
| Example 18 | Propanediol*2 | Squalane | Isopropyl myristate*14 | Cyclopentasiloxane*22 | Glyceryl (behenate/isostearate/eicosadioate)*23 |
| Example 19 | Diglycerin*3 | Hydrogenated polydecene*10 | Glycerol tri(caprylate/caprate)*15 | Dimethicone*20 | Glyceryl (behenate/isostearate/eicosadioate)*23 |
| Example 20 | PEG-20*4 | Hydrogenated polydecene*10 | Neopentyl glycol dicaprate*16 | Dimethicone*20 | Glyceryl (behenate/isostearate/eicosadioate)*23 |
| Example 21 | Sorbitol*5 | Hydrogenated polydecene*10 | Olive oil | Dimethicone*20 | Glyceryl (behenate/isostearate/eicosadioate)*23 |
| Example 22 | Trehalose*6 | Hydrogenated polydecene*10 | Macadamia nut oil*17 | Dimethicone*20 | Glyceryl (behenate/isostearate/eicosadioate)*23 |
| Example 23 | Sodium hyaluronate*7 | Hydrogenated polydecene*10 | Argania spinosa kernel oil*14 | Dimethicone*20 | Glyceryl (behenate/isostearate/eicosadioate)*23 |
| Example 24 | PPG-10 methyl glucose*8 | Hydrogenated polydecene*10 | Castor oil | Dimethicone*20 | Glyceryl (behenate/isostearate/eicosadioate)*23 |
| Example 25 | Methyl gluceth-10*9 | Hydrogenated polydecene*10 | Jojoba oil*19 | Dimethicone*20 | Glyceryl (behenate/eicosadioate)*24 |
| Comparative Example 10 | Glycerin | Hydrogenated polydecene*10 | Triethylhexanoin*12 | Dimethicone*20 | Glyceryl (behenate/isostearate/eicosadioate)*23 |
| Comparative Example 11 | Glycerin | Hydrogenated polydecene*10 | Triethylhexanoin*12 | Dimethicone*20 | Glyceryl (behenate/isostearate/eicosadioate)*23 |

*1"Adeka PG" (manufactured by Adeka Corporation)
*2"ZEMEA SELECT Propanediol" (manufactured by Zemea Co., Ltd.)
*3"Diglycerin 801" (manufactured by Sakamoto Yakuhin Kogyo Co., Ltd.)
*4"PEG #1000" (manufactured by NOF Corporation)
*5"SORBITOL KAO" (manufactured by Kao Corporation)
*6"Daily Trehalose for Cosmetics" (manufactured by Hayashibara Co., Ltd.)
*7"Hyaluronic Acid Q-5" (manufactured by Kewpie Corporation)
*8"GLUCAM P-10" (manufactured by Lubrizol Japan Limited)
*9"GLUCAM E-10" (manufactured by Lubrizol Japan Limited)
*10"NOMCORT HP-30" (manufactured by The Nisshin OilliO Group, Ltd.)
*11"CARNATION" (manufactured by Shima Trading Co., Ltd.)
*12"T.I.O" (manufactured by The Nisshin OilliO Group, Ltd.)
*13"SALACOS 99" (manufactured by The Nisshin OilliO Group, Ltd.)
*14"IPM" (manufactured by Kao Corporation)
*15"O.D.O" (manufactured by The Nisshin OilliO Group, Ltd.)
*16"ESTEMOL N-01" (manufactured by The Nisshin OilliO Group, Ltd.)
*17"Refined Macadamia Nut Oil" (manufactured by Yokozeki Oil & Fat Industries Co., Ltd.)
*18"Lipofructyl Argan LS 9779" (manufactured by LABORATOIRES SEROBIOLOGIQUES)
*19"Jojobal" (manufactured by Mitsuba Trading Co., Ltd.)
*20"KF-96A-10cs" (manufactured by Shin-Etsu Chemical Co., Ltd.)
*21"KF-56" (manufactured by Shin-Etsu Chemical Co., Ltd.)
*22"SH245 Fluid" (manufactured by Dow Corning Toray Co., Ltd.)
*23"NOMCORT SG" (manufactured by The Nisshin OilliO Group, Ltd.)
*24"NOMCORT HK-G" (manufactured by The Nisshin OilliO Group, Ltd.)

(Impression of Usability)

The "ease of scooping (scoopability) with a finger", "feeling of compatibility, as if to blend in, with the skin (skin compatibility)", "sliminess" and "freshness" of the samples of Example 16 and Comparative Examples 10 to 11 were evaluated in the same manner as in Example 1.

In addition, samples were applied to the entire face of 15 panelists, after washing the face, who were asked to answer the questionnaire regarding their impressions of usability of these samples, and the "oiliness" and "feeling of richness" of each sample were also evaluated in accordance with the following criteria.

"Oiliness"

a: 12 or more panelists answered that there was no oiliness.

b: 8 to 11 panelists answered that there was no oiliness.

c: 4 to 7 panelists answered that there was no oiliness.

d: 3 or less panelists answered that there was no oiliness.

"Feeling of Richness"

a: 12 or more panelists answered that there was a feeling of richness.

b: 8 to 11 panelists answered that there was a feeling of richness.

c: 4 to 7 panelists answered that there was a feeling of richness.

d: 3 or less panelists answered that there was a feeling of richness.

Furthermore, the "storage stability" of each sample was visually evaluated in accordance with the following criteria by degrees of water separation, oil separation and creaming after storage for 1 month at 50° C.

a: No water separation, oil separation or creaming was observed.

b: Any one of water separation, oil separation and creaming was observed.

TABLE 8

|  | Example | Comparative Examples | |
|---|---|---|---|
|  | 16 | 10 | 11 |
| Scoopability with a finger | a | c | a |
| Skin compatibility | a | d | b |
| Sliminess | a | a | d |
| Oiliness | a | a | d |
| Freshness | a | a | c |
| Feeling of richness | a | d | b |
| Storage stability | a | a | a |

The evaluation results are shown in Table 8. As a result, the oil-in-water emulsion type essence of Example 16 containing low molecular weight agar as the component (A), xanthan gum as the component (B) and a water-soluble polymer as the component (C) had no sliminess and oiliness, all of the scoopability with a finger, skin compatibility, freshness and feeling of richness were favorable, and the storage stability was also favorable. On the other hand, the oil-in-water emulsion type essence of Comparative Example 11 that did not contain a water-soluble polymer as the component (C) had sliminess and oiliness, although the scoopability with a finger was favorable, and the oil-in-water emulsion type essence of Comparative Example 10 that did not contain low molecular weight agar as the component (A) and xanthan gum as the component (B) was inferior in all of the scoopability with a finger, skin compatibility and feeling of richness.

Examples 26 to 32, Comparative Examples 12 to 13

In the formulations shown in Tables 9 and 10, all components were weighed in a beaker, mixed, heated to 85 to 95° C. to dissolve, and then cooled with stirring. A cream obtained as a result of degassing under reduced pressure was used as a sample. The same low molecular weight agar, xanthan gum and carboxyvinyl polymer as those used in Example 1, the same glycerin as that used in Example 11, the same hydrogenated polydecene, triethylhexanoin and dimethicone as those used in Example 16 and the same glyceryl tri(caprylate/caprate) as that used in Example 19 were used, respectively.

TABLE 9

|  |  | (% by mass) | | |
|---|---|---|---|---|
|  |  | Examples | Comparative Examples | |
|  |  | 26 to 32 | 12 | 13 |
| A | Low molecular weight agar | 0.18 | — | 0.18 |
| B | Xanthan gum | 0.12 | — | 0.12 |
| C | Carboxyvinyl polymer | 0.1 | 0.1 | — |

TABLE 9-continued

|  |  | (% by mass) | | |
|---|---|---|---|---|
|  |  | Examples | Comparative Examples | |
|  |  | 26 to 32 | 12 | 13 |
| D | Glycerin | 8 | 8 | 8 |
| D | 1,3-butylene glycol | 7.5 | 7.5 | 7.5 |
| D | Erythritol | 1 | 1 | 1 |
| E1 | Glyceryl stearate | 2.5 | 2.5 | 2.5 |
| E2 | Refer to Table 10 | 2.5 | 2.5 | 2.5 |
| F1 | Hydrogenated polydecene | 1 | 1 | 1 |
| F2 | Triethylhexanoin | 7 | 7 | — |
| F3 | Glyceryl tri(caprylate/caprate) | — | — | 6.5 |
| F4 | Dimethicone (10 cs) | 7.5 | 7.5 | 7.5 |
| F5 | Refer to Table 10 | 0.9 | 0.9 | 1.5 |
| G | Glyceryl tri(caprylate/caprate/myristate/stearate) | 2 | 2 | 2 |
| H | Microcrystalline wax | 1 | 1 | 1 |
| H | Cetanol | 3 | 3 | 3 |
| H | Stearyl alcohol | 1 | 1 | 1 |
| H | Behenyl alcohol | 0.7 | 0.7 | 0.7 |
|  | Phenoxyethanol | 0.1 | 0.1 | 0.1 |
|  | Methylparaben | 0.1 | 0.1 | 0.1 |
|  | Ethylparaben | 0.05 | 0.05 | 0.05 |
|  | Sodium hydroxide | 0.026 | 0.026 | — |
|  | Water | 53.724 | 54.024 | 53.75 |
| Total |  | 100 | 100 | 100 |

TABLE 10

|  | E2 | F5 |
|---|---|---|
| Example 26 | PEG-100 stearate*[1] | Dipentaerythrityl tripolyhydroxystearate*[8] |
| Example 27 | Polyglyceryl-2 oleate*[2] | Pentaerythrityl tetraethylhexanoate*[9] |
| Example 28 | Sorbitan sesquioleate*[3] | Diisostearyl malate*[10] |
| Example 29 | Sorbitan sesquiisostearate*[4] | Polyglyceryl-2 triisostearate*[11] |
| Example 30 | Steareth-20*[5] | Ethylhexyl hydroxystearate*[12] |
| Example 31 | PEG-11 methyl ether dimethicone*[6] | Di(phytosteryl/octyldodecyl) lauroyl glutamate*[13] |
| Example 32 | Cetearyl glucoside*[7] | Hydrogenated polyisobutene*[14] |
| Comparative Example 12 | PEG-100 stearate*[1] | Dipentaerythrityl tripolyhydroxystearate*[8] |
| Comparative Example 13 | PEG-100 stearate*[1] | Dipentaerythrityl tripolyhydroxystearate*[8] |

*[1]"EMALEX 8100" (manufactured by Nihon Emulsion Co., Ltd.)
*[2]"SALACOS DG-180" (manufactured by The Nisshin OilliO Group, Ltd.)
*[3]"COSMOL 82" (manufactured by The Nisshin OilliO Group, Ltd.)
*[4]"COSMOL 182V" (manufactured by The Nisshin OilliO Group, Ltd.)
*[5]"EMALEX 620" (manufactured by Nihon Emulsion Co., Ltd.)
*[6]"KF 6011" (manufactured by Shin-Etsu Chemical Co., Ltd.)
*[7]"TEGO Care CG 90" (manufactured by Evonik Goldschmidt GmbH)
*[8]"SALACOS WO-6" (manufactured by The Nisshin OilliO Group, Ltd.)
*[9]"SALACOS 5408" (manufactured by The Nisshin OilliO Group, Ltd.)
*[10]"COSMOL 222" (manufactured by The Nisshin OilliO Group, Ltd.)
*[11]"COSMOL 43V" (manufactured by The Nisshin OilliO Group, Ltd.)
*[12]"SALACOS EH" (manufactured by The Nisshin OilliO Group, Ltd.)
*[13]"Plandool-LG2" (manufactured by Nippon Fine Chemical Co., Ltd.)
*[14]"PARLEAM 18" (manufactured by NOF CORPORATION)

(Impression of Usability)

The "ease of scooping (scoopability) with a finger", "feeling of compatibility, as if to blend in, with the skin (skin compatibility)", "sliminess", "oiliness", "freshness", "feeling of richness" and "storage stability" of the samples of Example 26 and Comparative Examples 12 to 13 were evaluated in the same manner as in Example 16.

TABLE 11

|  | Example | Comparative Examples | |
|---|---|---|---|
|  | 26 | 12 | 13 |
| Scoopability with a finger | a | b | a |
| Skin compatibility | a | d | b |
| Sliminess | a | b | d |
| Oiliness | a | a | d |
| Freshness | a | a | c |
| Feeling of richness | a | c | a |
| Storage stability | a | a | d |

The evaluation results are shown in Table 11. As a result, the cream of Example 26 containing low molecular weight agar as the component (A), xanthan gum as the component (B) and a water-soluble polymer as the component (C) had no sliminess and oiliness, all of the scoopability with a finger, skin compatibility, freshness and feeling of richness were favorable, and the storage stability was also favorable. On the other hand, the cream of Comparative Example 13 that did not contain a water-soluble polymer as the component (C) had sliminess and oiliness, although the scoopability with a finger was favorable, and the cream of Comparative Example 12 that did not contain low molecular weight agar as the component (A) and xanthan gum as the component (B) lacked the skin compatibility and the feeling of richness was also absent.

Examples 33 to 39, Comparative Examples 14 to 15

In the formulations shown in Tables 12 and 13, all components were weighed in a beaker, mixed, heated to 85 to 95° C. to dissolve, and then cooled with stirring. A cream obtained as a result of degassing under reduced pressure was used as a sample. The same low molecular weight agar, xanthan gum and carboxyvinyl polymer as those used in Example 1, the same glycerin as that used in Example 11, the same hydrogenated polydecene, triethylhexanoin and dimethicone as those used in Example 16 and the same dipentaerythrityl tripolyhydroxystearate as that used in Example 26 were used, respectively.

TABLE 12

|  |  |  | (% by mass) | |
|---|---|---|---|---|
|  |  | Examples | Comparative Examples | |
|  |  | 33 to 39 | 14 | 15 |
| A | Low molecular weight agar | 0.60 |  | 0.60 |
| B | Xanthan gum | 0.40 |  | 0.40 |
| C | Carboxyvinyl polymer | 0.10 | 0.10 |  |
| D | Glycerin | 6.00 | 6.00 | 6.00 |
| D | 1,3-butylene glycol | 3.00 | 3.00 | 3.00 |
| E | Glyceryl stearate | 0.50 | 0.50 | 0.50 |
| E | PEG-10 stearate | 1.20 | 1.20 | 1.20 |
| F | Hydrogenated polydecene | 10.00 | 10.00 | 10.00 |
| F | Cetyl ethylhexanoate | 3.00 | 3.00 | 3.00 |
| F | Triethylhexanoin | 5.00 | 5.00 | 5.00 |
| F | Dipentaerythrityl tripolyhydroxystearate | 0.80 | 0.80 | 0.80 |
| F | Dimethicone | 3.50 | 3.50 | 3.50 |
| G1 | Refer to Table 13 | 3.00 | 3.00 | 3.00 |
| G2 | Refer to Table 13 | 1.00 | 1.00 | 1.00 |
| H | Polyglyceryl-10 (behenate/eicosadioate) | 2.00 | 2.00 | 2.00 |
| H | Cetanol | 2.50 | 2.50 | 2.50 |
| H | Behenyl alcohol | 0.50 | 0.50 | 0.50 |

TABLE 12-continued

|  |  | (% by mass) | |
|---|---|---|---|
|  | Examples | Comparative Examples | |
|  | 33 to 39 | 14 | 15 |
| Pentylene glycol | 2.50 | 2.50 | 2.50 |
| Methylparaben | 0.10 | 0.10 | 0.10 |
| Propylparaben | 0.05 | 0.05 | 0.05 |
| Ethylparaben | 0.05 | 0.05 | 0.05 |
| EDTA-2Na | 0.03 | 0.03 | 0.03 |
| Sodium hydroxide | 0.04 | 0.04 | 0.02 |
| Stearic acid | 1.00 | 1.00 | 1.00 |
| (Vinyl dimethicone/methicone silsesquioxane) crosspolymer | 0.50 | 0.50 | 0.50 |
| Water | 52.63 | 53.63 | 52.75 |
| Total | 100 | 100 | 100 |

TABLE 13

|  | G1 | G2 |
|---|---|---|
| Example 33 | Vaseline*[1] | Cholesteryl hydroxystearate*[2] |
| Example 34 | Lanolin | Hydrogenated palm oil*[6] |
| Example 35 | Purified lanolin | Hydrogenated coconut oil |
| Example 36 | phytosteryl oleate*[3] | Hydrogenated castor oil*[7] |
| Example 37 | Dipentaerythrityl tetra(hydroxystearate/isostearate)*[4] | Phytosteryl macadamiate*[8] |
| Example 38 | Dipentaerythrityl hexahydroxystearate*[5] | (Phytosteryl/isostearyl/cetyl/stearyl/behenyl) dimer dilinoleate*[9] |
| Example 39 | Vaseline*[1] | Di(phytosteryl/octyldodecyl/behenyl) lauroyl glutamate*[10] |
| Comparative Example 14 | Vaseline*[1] | Cholesteryl hydroxystearate*[2] |
| Comparative Example 15 | Vaseline*[1] | Cholesteryl hydroxystearate*[2] |

*[1]"NOMCORT W" (manufactured by The Nisshin OilliO Group, Ltd.)
*[2]"SALACOS HS" (manufactured by The Nisshin OilliO Group, Ltd.)
*[3]"SALACOS PO(T)" (manufactured by The Nisshin OilliO Group, Ltd.)
*[4]"COSMOL 168EV" (manufactured by The Nisshin OilliO Group, Ltd.)
*[5]"COSMOL 168M" (manufactured by The Nisshin OilliO Group, Ltd.)
*[6]"NOMCORT PHS" (manufactured by The Nisshin OilliO Group, Ltd.)
*[7]"CASTER WAX A FLAKE" (manufactured by NOF CORPORATION)
*[8]"Plandool-MAS" (manufactured by Nippon Fine Chemical Co., Ltd.)
*[9]"Plandool-H" (manufactured by Nippon Fine Chemical Co., Ltd.)
*[10]"Plandool-LG1" (manufactured by Nippon Fine Chemical Co., Ltd.)

(Impression of Usability)

The "ease of scooping (scoopability) with a finger", "feeling of compatibility, as if to blend in, with the skin (skin compatibility)", "sliminess", "oiliness", "freshness", "feeling of richness" and "storage stability" of the samples of Example 33 and Comparative Examples 14 to 15 were evaluated in the same manner as in Example 16.

TABLE 14

|  | Example | Comparative Examples | |
|---|---|---|---|
|  | 33 | 14 | 15 |
| Scoopability with a finger | a | b | a |
| Skin compatibility | a | d | b |
| Sliminess | a | b | d |
| Oiliness | a | a | d |
| Freshness | a | a | c |
| Feeling of richness | a | c | a |
| Storage stability | a | a | a |

The evaluation results are shown in Table 14. As a result, the cream of Example 33 containing low molecular weight agar as the component (A), xanthan gum as the component (B) and a water-soluble polymer as the component (C) had no sliminess and oiliness, all of the scoopability with a finger, skin compatibility, freshness and feeling of richness were favorable, and the storage stability was also favorable. On the other hand, the cream of Comparative Example 15 that did not contain a water-soluble polymer as the component (C) had sliminess and oiliness, although the scoopability with a finger was favorable, and the cream of Comparative Example 14 that did not contain low molecular weight agar as the component (A) and xanthan gum as the component (B) lacked the skin compatibility and the feeling of richness was also absent.

INDUSTRIAL APPLICABILITY

According to the present invention, it is possible to provide a water-based cosmetic that exhibits excellent scoopability with a finger, provides excellent feeling of richness and moist feeling while providing a highly fresh tactile sensation at the time of application to the skin, and provides a feeling of compatibility, as if to blend in, with the skin. Therefore, it is extremely useful industrially.

The invention claimed is:
1. A water-based cosmetic comprising:
    agar having a weight average molecular weight of 10,000 to 60,000 (component (A));
    xanthan gum (component (B)); and
    a water-soluble polymer excluding the component (A) or (B) (component (C)),
    wherein a ratio of a content of said component (A) to a content of said component (B) is from 4:6 to 8:2 in mass ratio;
    a ratio of a total content of said component (A) and said component (B) to a content of said component (C) is from 1:5 to 15:1 in mass ratio;
    the content of said component (A) is from 0.01 to 2% by mass with respect to a total mass of said water-based cosmetic;
    the content of said component (B) is from 0.01 to 2% by mass with respect to the total mass of said water-based cosmetic; and
    the content of said component (C) is from 0.01 to 2% by mass with respect to the total mass of said water-based cosmetic.
2. The water-based cosmetic according to claim 1, further comprising
    a moisturizing agent (component (D)) in an amount of 3 to 30% by mass with respect to the total mass of said water-based cosmetic.
3. The water-based cosmetic according to claim 1, further comprising
    a nonionic surfactant (component (E)) in an amount of 0.01 to 40% by mass with respect to the total mass of said water-based cosmetic.
4. The water-based cosmetic according to claim 1, further comprising
    an oil agent in a liquid form at 25° C. (component (F)) in an amount of 0.01 to 50% by mass with respect to the total mass of said water-based cosmetic.
5. The water-based cosmetic according to claim 1, further comprising
    an oil agent in a paste form at 25° C. (component (G)) in an amount of 0.01 to 10% by mass with respect to the total mass of said water-based cosmetic.
6. The water-based cosmetic according to claim 1, further comprising
    an oil agent in a solid form at 25° C. (component (H)) in an amount of 0.1 to 10% by mass with respect to the total mass of said water-based cosmetic.
7. The water-based cosmetic according to claim 1, wherein said component (C) is at least one selected from a carboxyvinyl polymer and an acrylic acid/alkyl methacrylate copolymer.
8. The water-based cosmetic according to claim 1, which is an oil-in-water type emulsion.

* * * * *